(12) United States Patent
Bae et al.

(10) Patent No.: US 7,901,902 B2
(45) Date of Patent: Mar. 8, 2011

(54) METHODS AND COMPOSITIONS FOR IDENTIFYING A CELLULAR IMMUNE RESPONSE AGAINST PROSTATE CANCER

(75) Inventors: Jooeun Bae, Vernon Hills, IL (US); Karin Jooss, Bellevue, WA (US)

(73) Assignee: BioSante Pharmaceuticals, Inc., Lincolnshire, IL (US)

( * ) Notice: Subject to any disclaimer, the term of this patent is extended or adjusted under 35 U.S.C. 154(b) by 365 days.

(21) Appl. No.: 11/881,808

(22) Filed: Jul. 26, 2007

(65) Prior Publication Data
US 2009/0053750 A1 Feb. 26, 2009

Related U.S. Application Data

(60) Provisional application No. 60/833,874, filed on Jul. 27, 2006.

(51) Int. Cl.
*C12Q 1/02* (2006.01)
*C07K 7/06* (2006.01)
*C07K 7/08* (2006.01)
*C12N 5/071* (2010.01)

(52) U.S. Cl. ........ 435/29; 435/372.3; 530/300; 530/327; 530/328

(58) Field of Classification Search .................... None
See application file for complete search history.

(56) References Cited

U.S. PATENT DOCUMENTS

| | | | |
|---|---|---|---|
| 5,637,483 | A | 6/1997 | Dranoff et al. |
| 5,904,920 | A | 5/1999 | Dranoff et al. |
| 5,985,290 | A | 11/1999 | Jaffee et al. |
| 6,033,674 | A | 3/2000 | Jaffee et al. |
| 6,277,368 | B1 | 8/2001 | Hiserodt et al. |
| 6,350,445 | B1 | 2/2002 | Jaffee et al. |
| 6,464,973 | B1 | 10/2002 | Levitsky et al. |
| 2006/0057127 | A1 | 3/2006 | Liu et al. |

FOREIGN PATENT DOCUMENTS

WO WO 2000/072686 A1 12/2000

OTHER PUBLICATIONS

Definition of Insect Cells from http://www.biochem.northwestern. edu/holmgren/Glossary/Definitions/Def-1/insect_cells.html, p. 1. Accessed Apr. 13, 2009.*
Immortalized Cells from http://www.microbiologybytes.com/video/culture.html, pp. 1-5. Accessed Apr. 13, 2009.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Introduction to Cancer from Merck manual, p. 1. Accessed Mar. 5, 2008.*
Clinical Aspects of Cancer from Merck manual, pp. 1-4. Accessed Mar. 5, 2008.*
Auerbach R, Akhtar N, Lewis RL, Shinners BL, "Angiogenesis assays: Problems and pitfalls," Cancer and Metastasis Reviews, 2000, 19: 167-172.*
Gura Trisha, "Systems for Identifying New Drugs Are Often Faulty," Science, 1997, 278: 1041-1042.*
Jain Rakesh K, "Barriers to Drug Delivery in Solid Tumors," Scientific American, Jul. 1994, 58-65.*
Abe et al., "Antitumor Effect Induced by Granulocyte/Macrophage-Colony-Stimulating Factor Gene-Modified Tumor Vaccination: Comparison of Adenovirus- and Retrovirus-Mediated Genetic Transduction," J. Cancer Res. Clin. Oncol., 121:587-592 (1995).
Altschul et al., "Basic Local Alignment Search Tool," J. Mol. Biol., 215:403-410 (1990).
Aoki et al., "Expression of Murine Interleukin 7 in a Murine Glioma Cell Line Results in Reduced Tumorigenicity in Vivo," Proc. Natl. Acad. Sci. USA, 89:3850-3854 (1992).
Armstrong et al., "Cytokine Modified Tumor Vaccines," Surg. Oncol. Clin. N. Am., 11:681-696 (2002).
Batzer et al., "Enhanced Evolutionary PCR Using Oligonucleotides with Inosine at the 3'-Terminus," Nucleic Acids Res., 19(18):5081 (1991).
Bodey et al., "Failure of Cancer Vaccines: The Significant Limitations of this Approach to Immunotherapy," Anticancer Res., 20:2665-2676 (2000).
Boon et al., "Cancer Tumor Antigens," Immunology, 9:681-683 (1997).
Borrello et al., "GM-CSF-Based Cellular Vaccines: A Review of the Clinical Experience," Cytokine & Growth Factor Reviews, 13:185-193 (2002).
Cantrell et al., "Cloning, Sequence, and Expression of a Human Granulocyte/Macrophage Colony-Stimulating Factor," Proc. Natl. Acad. Sci. USA, 82:6250-6254 (1985).
Chang et al., "Immunogenetic Therapy of Human Melanoma Utilizing Autologous Tumor Cells Transduced to Secrete Granulocyte-Macrophage Colony-Stimulating Factor," Human Gene Therapy, 11:839-850 (2000).
Darrow et al., "The Role of HLA Class I Antigens in Recognition of Melanoma Cells by Tumor-Specific Cytotoxic T Lymphocytes," J. of Immunology, 142(9):3329-3335 (1989).
Doytchinova et al., "EpiJen: A Server for Multistep T Cell Epitope Prediction," BMC Bioinformatics, 7:131, pp. 1-11 (2006).

(Continued)

*Primary Examiner* — Julie Ha
(74) *Attorney, Agent, or Firm* — Jones Day

(57) ABSTRACT

Filamin-B peptides, compositions comprising such peptides, and methods of using such peptides to assess an immune response against such peptides are described. An immune response against the peptides correlates with an immune response, in particular a cellular immune response, against prostate cancer cells which immune response is preferably associated with prophylaxis of prostate cancer, treatment of prostate cancer, and/or amelioration of at least one symptom associated with prostate cancer.

19 Claims, No Drawings

OTHER PUBLICATIONS

Dranoff et al., "Vaccination with Irradiated Tumor Cells Engineered to Secrete Murine Granulocyte-Macrophage Colony-Stimulating Factor Stimulates Potent, Specific, and Long-Lasting Anti-Tumor Immunity," Proc. Natl. Acad. Sci. USA, 90:3539-3543 (1993).

Fearon et al., "Interleukin-2 Production by Tumor Cells Bypasses T Helper Function in the Generation of an Antitumor Response," Cell, 60:397-403 (1990).

Forni et al., "Helper Strategy in Tumor Immunology: Expansion of Helper Lymphocytes and utilization of Helper Lymphokines for Experimental and Clinical Immunotherapy," Cancer and Metastasis Reviews, 7:289-309 (1988).

Gansbacher et al., "Retroviral Vector-Mediated γ-Interferon Gene Transfer into Tumor Cells Generates Potent and Long Lasting Anti-tumor Immunity," Cancer Research, 50:7820-7825 (1990).

Gansbacher et al., "Interleukin 2 Gene Transfer into Tumor Cells Abrogates Tumorigenicity and Induces Protective Immunity," J. Exp. Med., 172:1217-1224 (1990).

Gasson, "Molecular Physiology of Granulocyte-Macrophage Colony-Stimulating Factor," Blood, 77(6):1131-1145 (1991).

Golumbek et al., "Treatment of Established Renal Cancer by Tumor Cells Engineered to Secrete Interleukin-4," Science, 254:713-716 (1991).

Guan et al., "MHCPred 2.0: An Updated Quantitative T-Cell Epitope Prediction Server," Appl. Bioinformatics, 5(1):55-61 (2006).

Hattotuwagama et al., "Quantitative Online Prediction of Peptide Binding to the Major Histocompatibility Complex," J. Molecular Graphics and Modelling, 22:195-207 (2004).

Hock et al., "Interleukin 7 Induces CD4$^+$ T Cell-Dependent Tumor Rejection," J. Exp. Med., 174:1291-1298 (1991).

Hom et al., "Common Expression of Melanoma Tumor-Associated Antigens Recognized by Human Tumor Infiltrating Lymphocytes: Analysis by Human Lymphocyte Antigen Restriction," J. Immunotherapy, 10:153-164 (1991).

Huang et al., "Role of Bone Marrow-Derived Cells in Presenting MHC Class I-Restricted Tumor Antigens," Science, 264:961-965 (1994).

Huebner et al., "The Human Gene Encoding GM-CSF Is at 5q21-q32, the Chromosome Region Deleted in the 5q$^-$ Anomaly," Science, 230:1282-1285 (1985).

Jaffee et al., "Novel Allogeneic Granulocyte-Macrophage Colony-Stimulating Factor—Secreting Tumor Vaccine for Pancreatic Cancer: A Phase I Trial of Safety and Immune Activation," J. Clinical Oncology, 19(1):145-156 (2001).

Jaffee et al., "Gene Therapy: Its Potential Applications in the Treatment of Renal-Cell Carcinoma," Seminars in Oncology, 22(1):81-91 (1995).

Kawakami et al., "Shared Human Melanoma Antigens: Recognition by Tumor-Infiltrating Lymphocytes in HLA-A2.1-Transfected Melanomas," J. Of Immunology, 148(2):638-643 (1992).

Kesmir et al., "Prediction of Proteasome Cleavage Motifs by Neural Networks," Protein Engineering, 15(4):287-296 (2002).

Klein et al., "Properties of the K562 Cell Line, Derived from a Patient with Chronic Myeloid Leukemia," Int. J. Cancer, 18:421-431 (1976).

Lee et al., "Genetic Immunotherapy of Established Tumors with Adenovirus-Murine Granulocyte-Macrophage Colony-Stimulating Factor," Human Gene Therapy, 8:187-193 (1997).

Leedman et al., "Cloning from the Thyroid of a Protein Related to Actin Binding Protein that is Recognized by Graves Disease Immunoglobulins," Proc. Natl. Acad. Sci. USA, 90:5994-5998 (1993).

Lozzio et al., "Human Chronic Myelogenous Leukemia Cell-Line With Positive Philadelphia Chromosome," Blood, 45(3):321-334 (1975).

Mach et al., "Differences in Dendritic Cells Stimulated in Vivo by Tumors Engineered to Secrete Granulocyte-Macrophage Colony-Stimulating Factor or Flt3-Ligand," Cancer Research, 60:3239-3246 (2000).

Nagai et al., "Irradiated Tumor Cells Adenovirally Engineered to Secrete Granulocyte/Macrophage-Colony-Stimulating Factor Establish Antitumor Immunity and Eliminate Pre-Existing Tumors in Syngeneic Mice," Cancer Immunol. Immunother., 47:72-80 (1998).

Needleman et al., "A General Method Applicable to the Search for Similarities in the Amino Acid Sequence of Two Proteins," J. Mol. Biol., 48:443-453 (1970).

Nemunaitis et al., "Granulocyte-Macrophage Colony-Stimulating Factor Gene-Modified Autologous Tumor Vaccines in Non-Small-Cell Lung Cancer," J. Natl. Cancer Inst., 96(4):326-331 (2004).

Nielsen et al., "The Role of the Proteasome in Generating Cytotoxic T-Cell Epitopes: Insights Obtained from Improved Predictions of Proteasomal Cleavage," Immunogenetics, 57:33-41 (2005).

Oettgen et al., "The History of Cancer Immunotherapy," Biologic Therapy of Cancer, Chapter 6, pp. 87-119 (1991).

Ohtsuka et al., "An Alternative Approach to Deoxyoligonucleotides as Hybridization Probes by Insertion of Deoxyinosine at Ambiguous Codon Positions," J. Biological Chemistry, 260(5):2605-2608 (1985).

Pang et al., "Prostate Tissue Specificity of the Prostate-Specific Antigen Promoter Isolated from a Patient with Prostate Cancer," Human Gene Therapy, 6:1417-1426 (1995).

Pearson et al., "Improved Tools for Biological Sequence Comparison," Proc. Natl. Acad. Sci. USA, 85:2444-2448 (1988).

Porgador et al., "Immunotherapy of Tumor Metastasis via Gene Therapy," Nat. Immun., 13:113-130 (1994).

Pospisil et al., "A Combined Approach to Data Mining of Textual and Structured Data to Identify Cancer-Related Targets," BMC Bioinformatics, 7:354, pp. 1-11 (2006).

Rossolini et al., "Use of Deoxyinosine-Containing Primers vs Degenerate Primers for Polymerase Chain Reaction Based on Ambiguous Sequence Information," Molecular and Cellular Probes, 8:91-98 (1994).

Salgia et al., "Vaccination With Irradiated Autologous Tumor Cells Engineered to Secrete Granulocyte-Macrophage Colony-Stimulating Factor Augments Antitumor Immunity in Some Patients With Metastatic Non-Small-Cell Lung Carcinoma," J. Clinical Oncology, 21(4):624-630 (2003).

Sasson et al., "Functional Annotation Prediction: All for One and One for All," Protein Science, 15:1557-1562 (2006).

Sheen et al., "Filamin A and Filamin B Are Co-Expressed Within Neurons During Periods of Neuronal Migration and Can Physically Interact," Human Molecular Genetics, 11(23):2845-2854 (2002).

Simons et al., "Bioactivity of Autologous Irradiated Renal Cell Carcinoma Vaccines Generated by ex Vivo Granulocyte-Macrophage Colony-Stimulating Factor Gene Transfer," Cancer Research, 57:1537-1546 (1997).

Simons et al., "Induction of Immunity to Prostate Cancer Antigens: Results of a Clinical Trial of Vaccination with Irradiated Autologous Prostate Tumor Cells Engineered to Secrete Granulocyte-Macrophage Colony-Stimulating Factor Using ex Vivo Gene Transfer," Cancer Research, 59:5160-5168 (1999).

Smith et al., "Comparison of Biosequences," Advances in Applied Mathematics, 2:482-489 (1981).

Soiffer et al., "Vaccination With Irradiated, Autologous Melanoma Cells Engineered to Secrete Granulocyte-Macrophage Colony-Stimulating Factor by Adenoviral-Mediated Gene Transfer Augments Antitumor Immunity in Patients With Metastatic Melanoma," J. Clinical Oncology, 21(17):3343-3350 (2003).

Takafuta et al., "Human β-Filamin Is a New Protein That Interacts with the Cytoplasmic Tail of Glycoprotein Ibα," J. Biological Chemistry, 273(28):17531-17538 (1998).

Teng et al., "Long-Term Inhibition of Tumor Growth by Tumor Necrosis Factor in the Absence of Cachexia or T-Cell Immunity," Proc. Natl. Acad. Sci. USA, 88:3535-3539 (1991).

Thomas et al., "Mesothelin-Specific CD8$^+$ T Cell Responses Provide Evidence of in Vivo Cross-Priming by Antigen-Presenting Cells in Vaccinated Pancreatic Cancer Patients," J. Exp. Med., 200(3):297-306 (2004).

Van Der Flier et al., "Different Splice Variants of Filamin-B Affect Myogenesis, Subcellular Distribution, and Determine Binding to Integrin β Subunits," J. Cell Biology, 156(2):361-376 (2002).

Xu et al., "A Novel Human Actin-Binding Protein Homologue That Binds to Platelet Glycoprotein Ibα," Blood, 92(4):1268-1276 (1998).

* cited by examiner

SEQUENCE LISTING

```
<160> NUMBER OF SEQ ID NOS: 12

<210> SEQ ID NO 1
<211> LENGTH: 2602
<212> TYPE: PRT
<213> ORGANISM: Artificial Sequence
<220> FEATURE:
<223> OTHER INFORMATION: Filamin-B

<400> SEQUENCE: 1

Met Pro Val Thr Glu Lys Asp Leu Ala Glu Asp Ala Pro Trp Lys Lys
  1               5                  10                  15

Ile Gln Gln Asn Thr Phe Thr Arg Trp Cys Asn Glu His Leu Lys Cys
             20                  25                  30

Val Asn Lys Arg Ile Gly Asn Leu Gln Thr Asp Leu Ser Asp Gly Leu
         35                  40                  45

Arg Leu Ile Ala Leu Leu Glu Val Leu Ser Gln Lys Arg Met Tyr Arg
     50                  55                  60

Lys Tyr His Gln Arg Pro Thr Phe Arg Gln Met Gln Leu Glu Asn Val
 65                  70                  75                  80

Ser Val Ala Leu Glu Phe Leu Asp Arg Glu Ser Ile Lys Leu Val Ser
                 85                  90                  95

Ile Asp Ser Lys Ala Ile Val Asp Gly Asn Leu Lys Leu Ile Leu Gly
            100                 105                 110

Leu Val Trp Thr Leu Ile Leu His Tyr Ser Ile Ser Met Pro Val Trp
        115                 120                 125

Glu Asp Glu Gly Asp Asp Ala Lys Lys Gln Thr Pro Lys Gln Arg
    130                 135                 140

Leu Leu Gly Trp Ile Gln Asn Lys Ile Pro Tyr Leu Pro Ile Thr Asn
145                 150                 155                 160

Phe Asn Gln Asn Trp Gln Asp Gly Lys Ala Leu Gly Ala Leu Val Asp
                165                 170                 175

Ser Cys Ala Pro Gly Leu Cys Pro Asp Trp Glu Ser Trp Asp Pro Gln
            180                 185                 190

Lys Pro Val Asp Asn Ala Arg Glu Ala Met Gln Gln Ala Asp Asp Trp
        195                 200                 205

Leu Gly Val Pro Gln Val Ile Thr Pro Glu Glu Ile Ile His Pro Asp
    210                 215                 220

Val Asp Glu His Ser Val Met Thr Tyr Leu Ser Gln Phe Pro Lys Ala
225                 230                 235                 240

Lys Leu Lys Pro Gly Ala Pro Leu Lys Pro Lys Leu Asn Pro Lys Lys
                245                 250                 255

Ala Arg Ala Tyr Gly Arg Gly Ile Glu Pro Thr Gly Asn Met Val Lys
            260                 265                 270

Gln Pro Ala Lys Phe Thr Val Asp Thr Ile Ser Ala Gly Gln Gly Asp
        275                 280                 285

Val Met Val Phe Val Glu Asp Pro Glu Gly Asn Lys Glu Glu Ala Gln
    290                 295                 300
```

```
Val Thr Pro Asp Ser Asp Lys Asn Lys Thr Tyr Ser Val Glu Tyr Leu
305                 310                 315                 320

Pro Lys Val Thr Gly Leu His Lys Val Thr Val Leu Phe Ala Gly Gln
            325                 330                 335

His Ile Ser Lys Ser Pro Phe Glu Val Ser Val Asp Lys Ala Gln Gly
            340                 345                 350

Asp Ala Ser Lys Val Thr Ala Lys Gly Pro Gly Leu Glu Ala Val Gly
            355                 360                 365

Asn Ile Ala Asn Lys Pro Thr Tyr Phe Asp Ile Tyr Thr Ala Gly Ala
370                 375                 380

Gly Val Gly Asp Ile Gly Val Glu Val Glu Asp Pro Gln Gly Lys Asn
385                 390                 395                 400

Thr Val Glu Leu Leu Val Glu Asp Lys Gly Asn Gln Val Tyr Arg Cys
            405                 410                 415

Val Tyr Lys Pro Met Gln Pro Gly Pro His Val Val Lys Ile Phe Phe
            420                 425                 430

Ala Gly Asp Thr Ile Pro Lys Ser Pro Phe Val Val Gln Val Gly Glu
            435                 440                 445

Ala Cys Asn Pro Asn Ala Cys Arg Ala Ser Gly Arg Gly Leu Gln Pro
450                 455                 460

Lys Gly Val Arg Ile Arg Glu Thr Thr Asp Phe Lys Val Asp Thr Lys
465                 470                 475                 480

Ala Ala Gly Ser Gly Glu Leu Gly Val Thr Met Lys Gly Pro Lys Gly
            485                 490                 495

Leu Glu Glu Leu Val Lys Gln Lys Asp Phe Leu Asp Gly Val Tyr Ala
            500                 505                 510

Phe Glu Tyr Tyr Pro Ser Thr Pro Gly Arg Tyr Ser Ile Ala Ile Thr
            515                 520                 525

Trp Gly Gly His His Ile Pro Lys Ser Pro Phe Glu Val Gln Val Gly
530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
            565                 570                 575

Ser Glu Val Gly Ser Leu Gly Phe Ala Ile Glu Gly Pro Ser Gln Ala
            580                 585                 590

Lys Ile Glu Tyr Asn Asp Gln Asn Asp Gly Ser Cys Asp Val Lys Tyr
            595                 600                 605

Trp Pro Lys Glu Pro Gly Glu Tyr Ala Val His Ile Met Cys Asp Asp
610                 615                 620

Glu Asp Ile Lys Asp Ser Pro Tyr Met Ala Phe Ile His Pro Ala Thr
625                 630                 635                 640

Gly Gly Tyr Asn Pro Asp Leu Val Arg Ala Tyr Gly Pro Gly Leu Glu
            645                 650                 655

Lys Ser Gly Cys Ile Val Asn Asn Leu Ala Glu Phe Thr Val Asp Pro
            660                 665                 670

Lys Asp Ala Gly Lys Ala Pro Leu Lys Ile Phe Ala Gln Asp Gly Glu
            675                 680                 685

Gly Gln Arg Ile Asp Ile Gln Met Lys Asn Arg Met Asp Gly Thr Tyr
            690                 695                 700

Ala Cys Ser Tyr Thr Pro Val Lys Ala Ile Lys His Thr Ile Ala Val
705                 710                 715                 720

Val Trp Gly Gly Val Asn Ile Pro His Ser Pro Tyr Arg Val Asn Ile
```

-continued

```
                725                 730                 735
Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
            755                 760                 765

Cys Thr Glu Ala Gly Glu Gly Asp Val Ser Val Gly Ile Lys Cys Asp
            770                 775                 780

Ala Arg Val Leu Ser Glu Asp Glu Asp Val Asp Phe Asp Ile Ile
785                 790                 795                 800

His Asn Ala Asn Asp Thr Phe Thr Val Lys Tyr Val Pro Pro Ala Ala
                805                 810                 815

Gly Arg Tyr Thr Ile Lys Val Leu Phe Ala Ser Gln Glu Ile Pro Ala
                820                 825                 830

Ser Pro Phe Arg Val Lys Val Asp Pro Ser His Asp Ala Ser Lys Val
                835                 840                 845

Lys Ala Glu Gly Pro Gly Leu Ser Lys Ala Gly Val Glu Asn Gly Lys
            850                 855                 860

Pro Thr His Phe Thr Val Tyr Thr Lys Gly Ala Gly Lys Ala Pro Leu
865                 870                 875                 880

Asn Val Gln Phe Asn Ser Pro Leu Pro Gly Asp Ala Val Lys Asp Leu
                885                 890                 895

Asp Ile Ile Asp Asn Tyr Asp Tyr Ser His Thr Val Lys Tyr Thr Pro
                900                 905                 910

Thr Gln Gln Gly Asn Met Gln Val Leu Val Thr Tyr Gly Gly Asp Pro
            915                 920                 925

Ile Pro Lys Ser Pro Phe Thr Val Gly Val Ala Ala Pro Leu Asp Leu
            930                 935                 940

Ser Lys Ile Lys Leu Asn Gly Leu Glu Asn Arg Val Glu Val Gly Lys
945                 950                 955                 960

Asp Gln Glu Phe Thr Val Asp Thr Arg Gly Ala Gly Gly Gln Gly Lys
                965                 970                 975

Leu Asp Val Thr Ile Leu Ser Pro Ser Arg Lys Val Val Pro Cys Leu
            980                 985                 990

Val Thr Pro Val Thr Gly Arg Glu Asn Ser Thr Ala Lys Phe Ile Pro
            995                 1000                1005

Arg Glu Glu Gly Leu Tyr Ala Val Asp Val Thr Tyr Asp Gly His Pro
            1010                1015                1020

Val Pro Gly Ser Pro Tyr Thr Val Glu Ala Ser Leu Pro Pro Asp Pro
1025                1030                1035                1040

Ser Lys Val Lys Ala His Gly Pro Gly Leu Glu Gly Gly Leu Val Gly
                1045                1050                1055

Lys Pro Ala Glu Phe Thr Ile Asp Thr Lys Gly Ala Gly Thr Gly Gly
            1060                1065                1070

Leu Gly Leu Thr Val Glu Gly Pro Cys Glu Ala Lys Ile Glu Cys Ser
            1075                1080                1085

Asp Asn Gly Asp Gly Thr Cys Ser Val Ser Tyr Leu Pro Thr Lys Pro
            1090                1095                1100

Gly Glu Tyr Phe Val Asn Ile Leu Phe Glu Glu Val His Ile Pro Gly
1105                1110                1115                1120

Ser Pro Phe Lys Ala Asp Ile Glu Met Pro Phe Asp Pro Ser Lys Val
                1125                1130                1135

Val Ala Ser Gly Pro Gly Leu Glu His Gly Lys Val Gly Glu Ala Gly
            1140                1145                1150
```

-continued

Leu Leu Ser Val Asp Cys Ser Glu Ala Gly Pro Gly Ala Leu Gly Leu
        1155                1160            1165

Glu Ala Val Ser Asp Ser Gly Thr Lys Ala Glu Val Ser Ile Gln Asn
        1170            1175                1180

Asn Lys Asp Gly Thr Tyr Ala Val Thr Tyr Val Pro Leu Thr Ala Gly
1185                1190                1195                1200

Met Tyr Thr Leu Thr Met Lys Tyr Gly Gly Glu Leu Val Pro His Phe
            1205                1210                1215

Pro Ala Arg Val Lys Val Glu Pro Ala Val Asp Thr Ser Arg Ile Lys
        1220                1225                1230

Val Phe Gly Pro Gly Ile Glu Gly Lys Asp Val Phe Arg Glu Ala Thr
        1235                1240                1245

Thr Asp Phe Thr Val Asp Ser Arg Pro Leu Thr Gln Val Gly Gly Asp
        1250                1255                1260

His Ile Lys Ala His Ile Ala Asn Pro Ser Gly Ala Ser Thr Glu Cys
1265                1270                1275                1280

Phe Val Thr Asp Asn Ala Asp Gly Thr Tyr Gln Val Glu Tyr Thr Pro
            1285                1290                1295

Phe Glu Lys Gly Leu His Val Val Glu Val Thr Tyr Asp Asp Val Pro
        1300                1305                1310

Ile Pro Asn Ser Pro Phe Lys Val Ala Val Thr Glu Gly Cys Gln Pro
        1315                1320                1325

Ser Arg Val Gln Ala Gln Gly Pro Gly Leu Lys Glu Ala Phe Thr Asn
        1330                1335                1340

Lys Pro Asn Val Phe Thr Val Val Thr Arg Gly Ala Gly Ile Gly Gly
1345                1350                1355                1360

Leu Gly Ile Thr Val Glu Gly Pro Ser Glu Ser Lys Ile Asn Cys Arg
            1365                1370                1375

Asp Asn Lys Asp Gly Ser Cys Ser Ala Glu Tyr Ile Pro Phe Ala Pro
        1380                1385                1390

Gly Asp Tyr Asp Val Asn Ile Thr Tyr Gly Gly Ala His Ile Pro Gly
        1395                1400                1405

Ser Pro Phe Arg Val Pro Val Lys Asp Val Val Asp Pro Ser Lys Val
        1410                1415                1420

Lys Ile Ala Gly Pro Gly Leu Gly Ser Gly Val Arg Ala Arg Val Leu
1425                1430                1435                1440

Gln Ser Phe Thr Val Asp Ser Ser Lys Ala Gly Leu Ala Pro Leu Glu
            1445                1450                1455

Val Arg Val Leu Gly Pro Arg Gly Leu Val Glu Pro Val Asn Val Val
        1460                1465                1470

Asp Asn Gly Asp Gly Thr His Thr Val Thr Tyr Thr Pro Ser Gln Glu
        1475                1480                1485

Gly Pro Tyr Met Val Ser Val Lys Tyr Ala Asp Glu Glu Ile Pro Arg
        1490                1495                1500

Ser Pro Phe Lys Val Lys Val Leu Pro Thr Tyr Asp Ala Ser Lys Val
1505                1510                1515                1520

Thr Ala Ser Gly Pro Gly Leu Ser Ser Tyr Gly Val Pro Ala Ser Leu
            1525                1530                1535

Pro Val Asp Phe Ala Ile Asp Ala Arg Asp Ala Gly Glu Gly Leu Leu
        1540                1545                1550

Ala Val Gln Ile Thr Asp Gln Glu Gly Lys Pro Lys Arg Ala Ile Val
        1555                1560                1565

His Asp Asn Lys Asp Gly Thr Tyr Ala Val Thr Tyr Ile Pro Asp Lys
        1570                1575                1580

```
Thr Gly Arg Tyr Met Ile Gly Val Thr Tyr Gly Gly Asp Asp Ile Pro
1585                1590                1595                1600

Leu Ser Pro Tyr Arg Ile Arg Ala Thr Gln Thr Gly Asp Ala Ser Lys
                1605                1610                1615

Cys Leu Ala Thr Gly Pro Gly Ile Ala Ser Thr Val Lys Thr Gly Glu
                1620                1625                1630

Glu Val Gly Phe Val Val Asp Ala Lys Thr Ala Gly Lys Gly Lys Val
            1635                1640                1645

Thr Cys Thr Val Leu Thr Pro Asp Gly Thr Glu Ala Glu Ala Asp Val
1650                1655                1660

Ile Glu Asn Glu Asp Gly Thr Tyr Asp Ile Phe Tyr Thr Ala Ala Lys
1665                1670                1675                1680

Pro Gly Thr Tyr Val Ile Tyr Val Arg Phe Gly Gly Val Asp Ile Pro
                1685                1690                1695

Asn Ser Pro Phe Thr Val Met Ala Thr Asp Gly Glu Val Thr Ala Val
                1700                1705                1710

Glu Glu Ala Pro Val Asn Ala Cys Pro Pro Gly Phe Arg Pro Trp Val
            1715                1720                1725

Thr Glu Glu Ala Tyr Val Pro Val Ser Asp Met Asn Gly Leu Gly Phe
            1730                1735                1740

Lys Pro Phe Asp Leu Val Ile Pro Phe Ala Val Arg Lys Gly Glu Ile
1745                1750                1755                1760

Thr Gly Glu Val His Met Pro Ser Gly Lys Thr Ala Thr Pro Glu Ile
                1765                1770                1775

Val Asp Asn Lys Asp Gly Thr Val Thr Val Arg Tyr Ala Pro Thr Glu
                1780                1785                1790

Val Gly Leu His Glu Met His Ile Lys Tyr Met Gly Ser His Ile Pro
            1795                1800                1805

Glu Ser Pro Leu Gln Phe Tyr Val Asn Tyr Pro Asn Ser Gly Ser Val
            1810                1815                1820

Ser Ala Tyr Gly Pro Gly Leu Val Tyr Gly Val Ala Asn Lys Thr Ala
1825                1830                1835                1840

Thr Phe Thr Ile Val Thr Glu Asp Ala Gly Glu Gly Gly Leu Asp Leu
                1845                1850                1855

Ala Ile Glu Gly Pro Ser Lys Ala Glu Ile Ser Cys Ile Asp Asn Lys
                1860                1865                1870

Asp Gly Thr Cys Thr Val Thr Tyr Leu Pro Thr Leu Pro Gly Asp Tyr
            1875                1880                1885

Ser Ile Leu Val Lys Tyr Asn Asp Lys His Ile Pro Gly Ser Pro Phe
            1890                1895                1900

Thr Ala Lys Ile Thr Asp Asp Ser Arg Arg Cys Ser Gln Val Lys Leu
1905                1910                1915                1920

Gly Ser Ala Ala Asp Phe Leu Leu Asp Ile Ser Glu Thr Asp Leu Ser
                1925                1930                1935

Ser Leu Thr Ala Ser Ile Lys Ala Pro Ser Gly Arg Asp Glu Pro Cys
                1940                1945                1950

Leu Leu Lys Arg Leu Pro Asn Asn His Ile Gly Ile Ser Phe Ile Pro
            1955                1960                1965

Arg Glu Val Gly Glu His Leu Val Ser Ile Lys Lys Asn Gly Asn His
            1970                1975                1980

Val Ala Asn Ser Pro Val Ser Ile Met Val Val Gln Ser Glu Ile Gly
1985                1990                1995                2000

Asp Ala Arg Arg Ala Lys Val Tyr Gly Arg Gly Leu Ser Glu Gly Arg
```

-continued

Thr Phe Glu Met Ser Asp Phe Ile Val Asp Thr Arg Asp Ala Gly Tyr
2005                 2010                2015
                    2020                2025                2030

Gly Gly Ile Ser Leu Ala Val Glu Gly Pro Ser Lys Val Asp Ile Gln
            2035                2040                2045

Thr Glu Asp Leu Glu Asp Gly Thr Cys Lys Val Ser Tyr Phe Pro Thr
2050                2055                2060

Val Pro Gly Val Tyr Ile Val Ser Thr Lys Phe Ala Glu His Val
2065                2070                2075                2080

Pro Gly Ser Pro Phe Thr Val Lys Ile Ser Gly Glu Gly Arg Val Lys
            2085                2090                2095

Glu Ser Ile Thr Arg Thr Ser Arg Ala Pro Ser Val Ala Thr Val Gly
            2100                2105                2110

Ser Ile Cys Asp Leu Asn Leu Lys Ile Pro Glu Ile Asn Ser Ser Asp
            2115                2120                2125

Met Ser Ala His Val Thr Ser Pro Ser Gly Arg Val Thr Glu Ala Glu
            2130                2135                2140

Ile Val Pro Met Gly Lys Asn Ser His Cys Val Arg Phe Val Pro Gln
2145                2150                2155                2160

Glu Met Gly Val His Thr Val Ser Val Lys Tyr Arg Gly Gln His Val
            2165                2170                2175

Thr Gly Ser Pro Phe Gln Phe Thr Val Gly Pro Leu Gly Glu Gly Gly
            2180                2185                2190

Ala His Lys Val Arg Ala Gly Gly Pro Gly Leu Glu Arg Gly Glu Ala
            2195                2200                2205

Gly Val Pro Ala Glu Phe Ser Ile Trp Thr Arg Glu Ala Gly Ala Gly
            2210                2215                2220

Gly Leu Ser Ile Ala Val Glu Gly Pro Ser Lys Ala Glu Ile Thr Phe
2225                2230                2235                2240

Asp Asp His Lys Asn Gly Ser Cys Gly Val Ser Tyr Ile Ala Gln Glu
            2245                2250                2255

Pro Gly Asn Tyr Glu Val Ser Ile Lys Phe Asn Asp Glu His Ile Pro
            2260                2265                2270

Glu Ser Pro Tyr Leu Val Pro Val Ile Ala Pro Ser Asp Asp Ala Arg
            2275                2280                2285

Arg Leu Thr Val Met Ser Leu Gln Glu Ser Gly Leu Lys Val Asn Gln
            2290                2295                2300

Pro Ala Ser Phe Ala Ile Arg Leu Asn Gly Ala Lys Gly Lys Ile Asp
2305                2310                2315                2320

Ala Lys Val His Ser Pro Ser Gly Ala Val Glu Glu Cys His Val Ser
            2325                2330                2335

Glu Leu Glu Pro Asp Lys Tyr Ala Val Arg Phe Ile Pro His Glu Asn
            2340                2345                2350

Gly Val His Thr Ile Asp Val Lys Phe Asn Gly Ser His Val Val Gly
            2355                2360                2365

Ser Pro Phe Lys Val Arg Val Gly Glu Pro Gly Gln Ala Gly Asn Pro
            2370                2375                2380

Ala Leu Val Ser Ala Tyr Gly Thr Gly Leu Glu Gly Gly Thr Thr Gly
            2385                2390                2395                2400

Ile Gln Ser Glu Phe Phe Ile Asn Thr Thr Arg Ala Gly Pro Gly Thr
            2405                2410                2415

Leu Ser Val Thr Ile Glu Gly Pro Ser Lys Val Lys Met Asp Cys Gln
            2420                2425                2430

-continued

```
Glu Thr Pro Glu Gly Tyr Lys Val Met Tyr Thr Pro Met Ala Pro Gly
        2435                2440                2445

Asn Tyr Leu Ile Ser Val Lys Tyr Gly Gly Pro Asn His Ile Val Gly
    2450                2455                2460

Ser Pro Phe Lys Ala Lys Val Thr Gly Gln Arg Leu Val Ser Pro Gly
2465                2470                2475                2480

Ser Ala Asn Glu Thr Ser Ser Ile Leu Val Glu Ser Val Thr Arg Ser
            2485                2490                2495

Ser Thr Glu Thr Cys Tyr Ser Ala Ile Pro Lys Ala Ser Ser Asp Ala
        2500                2505                2510

Ser Lys Val Thr Ser Lys Gly Ala Gly Leu Ser Lys Ala Phe Val Gly
        2515                2520                2525

Gln Lys Ser Ser Phe Leu Val Asp Cys Ser Lys Ala Gly Ser Asn Met
    2530                2535                2540

Leu Leu Ile Gly Val His Gly Pro Thr Thr Pro Cys Glu Glu Val Ser
2545                2550                2555                2560

Met Lys His Val Gly Asn Gln Gln Tyr Asn Val Thr Tyr Val Val Lys
            2565                2570                2575

Glu Arg Gly Asp Tyr Val Leu Ala Val Lys Trp Gly Gly Glu His Ile
        2580                2585                2590

Pro Gly Ser Pro Phe His Val Thr Val Pro
        2595                2600

<210> SEQ ID NO 2
<211> LENGTH: 9
<212> TYPE: PRT
<213> ORGANISM: Artificial Sequence
<220> FEATURE:
<223> OTHER INFORMATION: Filamin-B peptides

<400> SEQUENCE: 2

Leu Ile Leu Gly Leu Val Trp Thr Leu
  1               5

<210> SEQ ID NO 3
<211> LENGTH: 9
<212> TYPE: PRT
<213> ORGANISM: Artificial Sequence
<220> FEATURE:
<223> OTHER INFORMATION: Filamin-B peptides

<400> SEQUENCE: 3

Gly Leu Val Glu Pro Val Asn Met Val
  1               5

<210> SEQ ID NO 4
<211> LENGTH: 9
<212> TYPE: PRT
<213> ORGANISM: Artificial Sequence
<220> FEATURE:
<223> OTHER INFORMATION: Filamin-B peptides

<400> SEQUENCE: 4

Gly Leu Ala Pro Leu Glu Val Arg Val
  1               5

<210> SEQ ID NO 5
<211> LENGTH: 9
<212> TYPE: PRT
<213> ORGANISM: Artificial Sequence
<220> FEATURE:
<223> OTHER INFORMATION: Filamin-B peptides
```

-continued

<400> SEQUENCE: 5

Ser Leu Gln Glu Ser Gly Leu Lys Val
1               5

<210> SEQ ID NO 6
<211> LENGTH: 9
<212> TYPE: PRT
<213> ORGANISM: Artificial Sequence
<220> FEATURE:
<223> OTHER INFORMATION: Filamin-B peptides

<400> SEQUENCE: 6

Arg Leu Ile Ala Leu Leu Glu Val Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Filamin-B peptides

<400> SEQUENCE: 7

Gly Gln Gly Asp Val Met Val Phe Val
1               5

<210> SEQ ID NO 8
<211> LENGTH: 9
<212> TYPE: PRT
<213> ORGANISM: Artificial Sequence
<220> FEATURE:
<223> OTHER INFORMATION: Filamin-B peptides

<400> SEQUENCE: 8

Lys Leu Ile Leu Gly Leu Val Trp Thr
1               5

<210> SEQ ID NO 9
<211> LENGTH: 2027
<212> TYPE: DNA
<213> ORGANISM: Homo Sapiens

<400> SEQUENCE: 9

```
tgtggctgca gagcctgctg ctcttgggca ctgtggcctg cagcatctct gcacccgccc      60
gctcgcccag ccccagcacg cagccctggg agcatgtgaa tgccatccag gaggcccggc     120
gtctcctgaa cctgagtaga gacactgctg ctgagatggt aagtgagaga atgtgggcct     180
gtgcctaggc cacccagctg gcccctgact ggccacgcct gtcagcttga taacatgaca     240
ttttcctttt ctacagaatg aaacagtaga agtcatctca gaaatgtttg acctccaggt     300
aagatgcttc tctctgacat agctttccag aagcccctgc cctggggtgg aggtggggac     360
tccatttag  atggcaccac acagggttgt ccactttctc tccagtcagc tggctgcagg     420
aggaggggt  agcaactggg tgctcaagag gctgctggcc gtgcccctat ggcagtcaca     480
tgagctcctt tatcagctga gcggccatgg gcagacctag cattcaatgg ccaggagtca     540
ccaggggaca ggtggtaaag tgggggtcac ttcatgagac aggagctgtg ggtttgggc      600
gctcactgtg ccccgagacc aagtcctgtt gagacagtgc tgactacaga gaggcacaga     660
ggggtttcag gaacaaccct tgcccaccca gcaggtccag gtgaggcccc accccctct      720
ccctgaatga tggggtgaga gtcacctcct ccctaaggc  tgggctcctc tccaggtgcc     780
gctgagggtg gcctgggcgg ggcagtgaga agggcaggtt cgtgcctgcc atggacaggg     840
```

```
cagggtctat gactggaccc agcctgtgcc cctcccaagc cctactcctg ggggctgggg    900
gcagcagcaa aaaggagtgg tggagagttc ttgtaccact gtgggcactt ggccactgct    960
caccgacgaa cgacattttc cacaggagcc gacctgccta cagacccgcc tggagctgta   1020
caagcagggc ctgcggggca gcctcaccaa gctcaagggc cccttgacca tgatggccag   1080
ccactacaag cagcactgcc ctccaacccc ggtgagtgcc tacggcaggg cctccagcag   1140
gaatgtctta atctaggggg tggggtcgac atggggagag atctatggct gtggctgttc   1200 aggacccag ggggtttctg tgccaacagt tatgtaatga ttagccctcc agagaggagg   1260
cagacagccc atttcatccc aaggagtcag agccacagag cgctgaagcc cacagtgctc   1320
cccagcagga gctgctccta tcctggtcat tattgtcatt atggttaatg aggtcagagg   1380
tgagggcaaa cccaaggaaa cttggggcct gccaaggcc cagaggaagt gcccaggccc   1440
aagtgccacc ttctggcagg actttcctct ggccccacat ggggtgcttg aattgcagag   1500
gatcaaggaa gggggctac ttggaatgga caaggacctc aggcactcct tcctgcggga   1560
agggagcaaa gtttgtggcc ttgactccac tccttctggg tgcccagaga cgacctcagc   1620
ccagctgccc tgctctgccc tgggaccaaa aaggcaggcg tttgactgcc cagaaggcca   1680
acctcaggct ggcacttaag tcaggccctt gactctggct gccactggca gagctatgca   1740
ctccttgggg aacacgtggg tggcagcagc gtcacctgac ccaggtcagt gggtgtgtcc   1800
tggagtgggc ctcctggcct ctgagttcta agaggcagta gagaaacatg ctggtgcttc   1860
cttcccccac gttacccact tgcctggact caagtgtttt ttattttcct tttttaaag   1920 gaaacttcct gtgcaaccca gattatcacc tttgaaagtt tcaaagagaa cctgaaggac   1980
tttctgcttg tcatcccctt tgactgctgg gagccagtcc aggagtg                2027
```

```
<210> SEQ ID NO 10
<211> LENGTH: 435
<212> TYPE: DNA
<213> ORGANISM: Homo Sapiens

<400> SEQUENCE: 10
atgtggctgc agagcctgct gctcttgggc actgtggcct gcagcatctc tgcacccgcc     60
cgctcgccca gccccagcac gcagccctgg gagcatgtga atgccatcca ggaggcccgg    120
cgtctcctga actgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaagcagc actgccctcc aaccccggaa acttcctgtg caacccagac tatcaccttt    360
gaaagtttca agagaaacct gaaggacttt ctgcttgtca tcccctttga ctgctgggag    420
ccagtccagg agtaa                                                     435
```

```
<210> SEQ ID NO 11
<211> LENGTH: 144
<212> TYPE: PRT
<213> ORGANISM: Homo Sapiens

<400> SEQUENCE: 11

Met Trp Leu Gln Ser Leu Leu Leu Gly Thr Val Ala Cys Ser Ile
 1               5                  10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45
```

-continued

```
Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Thr Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 12
<211> LENGTH: 9
<212> TYPE: PRT
<213> ORGANISM: Artificial Sequence
<220> FEATURE:
<223> OTHER INFORMATION: Filamin-B peptides

<400> SEQUENCE: 12

Gly Ile Leu Gly Phe Val Phe Thr Leu
1               5
```

US 7,901,902 B2

METHODS AND COMPOSITIONS FOR IDENTIFYING A CELLULAR IMMUNE RESPONSE AGAINST PROSTATE CANCER

1. CROSS-REFERENCE TO RELATED APPLICATION

This application is entitled to and claims benefit of U.S. Provisional Application No. 60/833,874, filed Jul. 27, 2006, which is hereby incorporated by reference in its entirety.

2. FIELD OF THE INVENTION

The present invention relates to filamin-B peptides, compositions comprising such peptides, and methods of using such peptides to assess an immune response against such peptides. An immune response against the peptides correlates with an immune response, in particular a cellular immune response, against prostate cancer cells which immune response is preferably associated with prophylaxis of prostate cancer, treatment of prostate cancer, and/or amelioration of at least one symptom associated with prostate cancer.

3. BACKGROUND

The immune system plays a critical role in the pathogenesis of a wide variety of cancers. When cancers progress, it is widely believed that the immune system either fails to respond sufficiently or fails to respond appropriately, allowing cancer cells to grow. Currently, standard medical treatments for cancer including chemotherapy, surgery, radiation therapy and cellular therapy have clear limitations with regard to both efficacy and toxicity. To date, these approaches have met with varying degrees of success dependent upon the type of cancer, general health of the patient, stage of disease at the time of diagnosis, etc. Improved strategies that combine specific manipulation of the immune response to cancer in combination with standard medical treatments may provide a means for enhanced efficacy and decreased toxicity.

One therapeutic approach to cancer treatment involves the use of genetically modified tumor cells which express cytokines locally at the vaccine site. Activity has been demonstrated in tumor models using a variety of immunomodulatory cytokines, including IL-4, IL-2, TNF-alpha, G-CSF, IL-7, IL-6 and GM-CSF, as described in Golumbeck P T et al., Science 254:13-716, 1991; Gansbacher B et al., J. Exp. Med. 172:1217-1224, 1990; Fearon E R et al., Cell 60:397-403, 1990; Gansbacher B et al., Cancer Res. 50:7820-25, 1990; Teng M et al., PNAS 88:3535-3539, 1991; Columbo M P et al., J. Exp. Med. 174:1291-1298, 1991; Aoki et al., Proc Natl Acad Sci USA. 89(9):3850-4, 1992; Porgador A, et al., Nat. Immun. 13(2-3):113-30, 1994; Dranoff G et al., PNAS 90:3539-3543, 1993; Lee C T et al., Human Gene Therapy 8:187-193, 1997; Nagai E et al., Cancer Immunol. Immonther. 47:2-80, 1998 and Chang A et al., Human Gene Therapy 11:839-850, 2000, respectively. The use of autologous cancer cells as vaccines to augment anti-tumor immunity has been explored for some time. See, e.g., Oettgen et al., "The History of Cancer Immunotherapy", In: Biologic Therapy of Cancer, Devita et al. (eds.) J. Lippincot Co., pp 87-199, 1991; Armstrong T D and Jaffee E M, Surg Oncol Clin N Am. 11(3):681-96, 2002; and Bodey B et al., Anticancer Res 20(4):2665-76, 2000).

Several phase I/II human trials using GM-CSF-secreting autologous or allogeneic tumor cell vaccines have been performed (Simons et al. Cancer Res 1999 59:5160-8; Soiffer et al. Proc Natl Acad Sci USA 1998 95:13141-6; Simons et al. Cancer Res 1997 57:1537-46; Jaffee et al. J Clin Oncol 2001 19:145-56; Salgia et al. Clin Oncol 2003 21:624-30; Soiffer et al. J Clin Oncol 2003 21:3343-50; Nemunaitis et al. J Natl Cancer Inst. 2004 Feb. 18 96(4):326-31; Borello and Pardoll, Growth Factor Rev. 13(2):185-93, 2002; and Thomas et al., J. Exp. Med. 200(3)297-306, 2004).

Administration of genetically modified GM-CSF-expressing cancer cells to a patient results in an immune response and preliminary clinical efficacy against prostate and other cancers has been demonstrated in Phase I/II clinical trails. However, there remains a need for improved methods and compositions for predicting whether such therapies are likely to be effective, for monitoring the effectiveness of such therapies, and for increasing the effectiveness of such therapies. These and other needs are provided by the present invention.

4. SUMMARY

The present invention provides filamin-B peptides, compositions comprising such peptides, kits comprising the peptides, and methods of using the peptides. The peptides are useful, for example, for assessing the cellular immune response following cancer therapy with genetically modified tumor cells that express a cytokine, e.g., GM-CSF.

Accordingly, in a first aspect, the invention provides an isolated peptide comprising about 8 to about 12 contiguous amino acids of filamin-B (SEQ ID NO:1), wherein said amino acids bind to class I MHC, e.g., HLA-A2 under physiological conditions.

In another aspect, the invention provides a composition comprising an isolated peptide comprising about 8 to about 12 contiguous amino acids of filamin-B (SEQ ID NO:1), wherein said amino acids bind to HLA-A2 under physiological conditions.

In still another aspect, the invention provides a method for determining whether a cellular immune response against cancer cells has been induced in a subject, comprising contacting cytotoxic T lymphocytes (CTLs) from the subject to cells that express an HLA-A2 class I MHC receptor, wherein the HLA-A2 receptor has a peptide comprising about 8 to about 12 amino acids selected from a filamin-B polypeptide (SEQ ID NO:1) bound thereto; and detecting activation of the CTLs by the cells that express the HLA-A2 receptor, wherein detecting said activation indicates that a cellular immune response against prostate cancer cells has been induced in the subject.

In yet another aspect, the invention provides a method for determining whether a cellular immune response effective to treat, prevent, or ameliorate a symptom of prostate cancer in a subject has been induced in the subject, comprising contacting, in vitro, CTLs from the subject to cells that express an HLA-A2 class I MHC receptor, wherein the HLA-A2 receptor has a peptide comprising about 8 to about 12 amino acids selected from a filamin-B polypeptide (SEQ ID NO:1) bound thereto; and detecting activation of the CTLs by the cells that express the HLA-A2 receptor, wherein detecting said activation indicates that a cellular immune response effective to treat, prevent, or ameliorate a symptom of prostate cancer has been induced in the subject.

In still another aspect, the invention provides a method for determining whether a subject afflicted with prostate cancer is likely to respond to treatment with genetically modified tumor cells that produce GM-CSF, comprising contacting CTLs from the subject to cells that express an HLA-A2 class I MHC receptor, wherein the HLA-A2 receptor has a peptide comprising about 8 to about 12 amino acids selected from a filamin-B polypeptide (SEQ ID NO:1) bound thereto; and detecting activation of the CTLs by the cells that express the HLA-A2 receptor, wherein detecting said activation indicates that subject afflicted with prostate cancer is likely to respond to treatment with genetically modified tumor cells that produce GM-CSF.

In yet another aspect, the invention provides a method for generating CTLs that are activated by cells expressing HLA-A2 class I MHC having a peptide comprising about 8 to about 12 amino acids selected from a filamin-B polypeptide (SEQ ID NO:1) bound thereto, comprising contacting a population of CTLs with cells expressing HLA-A2 class I MHC having a peptide comprising about 8 to about 12 amino acids selected from a filamin-B polypeptide (SEQ ID NO:1) bound thereto; identifying one or more CTLs from the population that are activated by the contact; and isolating said one or more CTLs.

In still another aspect, the invention provides method for assessing the effectiveness of prostate cancer therapy with genetically modified tumor cells that express GM-CSF to treat or ameliorate a symptom of prostate cancer of a subject in need thereof, comprising administering genetically modified tumor cells that express GM-CSF to the subject; isolating CTLs from the subject; and determining whether the CTLs are activated by contacting cells that express the HLA-A2 receptor class I MHC having a peptide comprising about 8 to about 12 amino acids selected from a filamin-B polypeptide (SEQ ID NO:1) bound thereto, wherein activation indicates that the treatment with genetically modified tumor cells that produce GM-CSF is effective to treat or ameliorate a symptom of prostate cancer in said subject.

In yet another aspect, the invention provides a kit, comprising a first container containing a peptide comprising about 8 to about 12 amino acids selected from a filamin-B polypeptide (SEQ ID NO:1), wherein said peptide binds to HLA-A2, and a second container containing cells expressing HLA-A2 class I MHC.

The present invention provides filamin-B peptides, compositions comprising such peptides, kits comprising the peptides, and methods of using the peptides. The peptides are useful, for example, for assessing the cellular immune response following cancer therapy with genetically modified tumor cells that express a cytokine, e.g., GM-CSF.

Without intending to be bound to any particular theory or mechanism of action, it is believed that one aspect of the immune response induced by therapy with genetically modified tumor cells that express a cytokine is an immune response against filamin-B. The humoral component of this immune response, and the importance of this immune response in effectively treating cancer, is extensively discussed in U.S. Patent Application Publication No. 2006/0057127. It is also believed that the cellular component of this immune response, e.g., lysis of cells that display filamin-B antigen by CTLs, plays an important role in the effectiveness of this therapy to treat cancer, e.g., prostate cancer. Accordingly, the present invention provides filamin-B peptides that can be presented via class I MHC molecules to CTLs, thereby activating the CTLs, as well as numerous compositions, methods, and kits relating thereto.

5.1 DEFINITIONS

By the term "cytokine" or grammatical equivalents, herein is meant the general class of hormones of the cells of the immune system, including lymphokines, monokines, and others. The definition includes, without limitation, those hormones that act locally and do not circulate in the blood, and which, when used in accord with the present invention, will result in an alteration of an individual's immune response. The term "cytokine" or "cytokines" as used herein refers to the general class of biological molecules, which affect cells of the immune system. The definition is meant to include, but is not limited to, those biological molecules that act locally or may circulate in the blood, and which, when used in the compositions or methods of the present invention serve to regulate or modulate an individual's immune response to cancer. Exemplary cytokines for use in practicing the invention include, but are not limited to, interferon-alpha (IFN-alpha), IFN-beta, and IFN-gamma, interleukins (e.g., IL-1 to IL-29, in particular, IL-2, IL-7, IL-12, IL-15 and IL-18), tumor necrosis factors (e.g., TNF-alpha and TNF-beta), erythropoietin (EPO), MIP3a, ICAM, macrophage colony stimulating factor (M-CSF), granulocyte colony stimulating factor (G-CSF) and granulocyte-macrophage colony stimulating factor (GM-CSF).

As used herein, the terms "cancer", "cancer cells", "neoplastic cells", "neoplasia", "tumor", and "tumor cells" (used interchangeably) refer to cells that exhibit relatively autonomous growth, so that they exhibit an aberrant growth phenotype or aberrant cell status characterized by a significant loss of control of cell proliferation. A tumor cell may be a hyperplastic cell, a cell that shows a lack of contact inhibition of growth in vitro or in vivo, a cell that is incapable of metastasis in vivo, or a cell that is capable of metastasis in vivo. Neoplastic cells can be malignant or benign. It follows that cancer cells are considered to have an aberrant cell status. "Tumor cells" may be derived from a primary tumor or derived from a tumor metastases. The "tumor cells" may be recently isolated from a patient (a "primary tumor cell") or may be the product of long term in vitro culture.

The term "primary tumor cell" is used in accordance with the meaning in the art. A primary tumor cell is a cancer cell that is isolated from a tumor in a mammal and has not been extensively cultured in vitro.

The term "antigen from a tumor cell" and "tumor antigen" and "tumor cell antigen" may be used interchangeably herein and refer to any protein, peptide, carbohydrate or other component derived from or expressed by a tumor cell which is capable of eliciting an immune response. The definition is meant to include, but is not limited to, whole tumor cells, tumor cell fragments, plasma membranes taken from a tumor cell, proteins purified from the cell surface or membrane of a tumor cell, unique carbohydrate moieties associated with the cell surface of a tumor cell or tumor antigens expressed from a vector in a cell. The definition also includes those antigens from the surface of the cell, which require special treatment of the cells to access.

The term "genetically modified tumor cell" as used herein refers to a composition comprising a population of cells that has been genetically modified to express a transgene, and that is administered to a patient as part of a cancer treatment regimen. The genetically modified tumor cell vaccine comprises tumor cells which are "autologous" or "allogeneic" to the patient undergoing treatment or "bystander cells" that are mixed with tumor cells taken from the patient. Generally, the genetically modified tumor cell is of the same general type of tumor cell as is afflicting the patient, e.g., if the patient is afflicted with metastatic prostate cancer, the genetically modified tumor cell is also a metastatic prostate cancer cell. A GM-CSF-expressing genetically modified tumor cell vaccine may be referred to herein as "GVAX"®. Autologous and allogeneic cancer cells that have been genetically modified to express a cytokine, e.g., GM-CSF, followed by readministration to a patient for the treatment of cancer are described in U.S. Pat. Nos. 5,637,483, 5,904,920, 6,277,368 and 6,350,445, each of which is expressly incorporated by reference herein. A form of GM-CSF-expressing genetically modified cancer cells or a "cytokine-expressing cellular vaccine" for the treatment of pancreatic cancer is described in U.S. Pat. Nos. 6,033,674 and 5,985,290, both of which are expressly incorporated by reference herein. A universal immunomodulatory cytokine-expressing bystander cell line is described in U.S. Pat. No. 6,464,973, expressly incorporated by reference herein.

The term "enhanced expression" as used herein, refers to a cell producing higher levels of a particular protein than would be produced by the naturally occurring cell or the parental cell from which it was derived. Cells may be genetically modified to increase the expression of a cytokine, such as GM-CSF, or an antigen the immune response to which is enhanced following administration of a cytokine-expressing cellular vaccine, such as GVAX®. The expression of an endogenous antigen may be increased using any method known in the art, such as genetically modifying promoter regions of genomic sequences or genetically altering cellular signaling pathways to increase production of the antigen. Also, cells can be transduced with a vector coding for the antigen or immunogenic fragment thereof.

By the term "systemic immune response" or grammatical equivalents herein is meant an immune response which is not localized, but affects the individual as a whole, thus allowing specific subsequent responses to the same stimulus.

As used herein, the term "proliferation-incompetent" or "inactivated" refers to cells that are unable to undergo multiple rounds of mitosis, but still retain the capability to express proteins such as cytokines or tumor antigens. This may be achieved through numerous methods known to those skilled in the art. Embodiments of the invention include, but are not limited to, treatments that inhibit at least about 95%, at least about 99% or substantially 100% of the cells from further proliferation. In one embodiment, the cells are irradiated at a dose of from about 50 to about 200 rads/min or from about 120 to about 140 rads/min prior to administration to the mammal. Typically, when using irradiation, the levels required are 2,500 rads, 5,000 rads, 10,000 rads, 15,000 rads or 20,000 rads. In several embodiments of the invention the cells produce beta-filamin or immunogenic fragment thereof, two days after irradiation, at a rate that is at least about 10%, at least about 20%, at least about 50% or at least about 100% of the pre-irradiated level, when standardized for viable cell number. In one embodiment of the invention, cells are rendered proliferation incompetent by irradiation prior to administration to the subject.

By the term "individual", "subject" or grammatical equivalents thereof is meant any one individual mammal.

By the term "reversal of an established tumor" or grammatical equivalents herein is meant the suppression, regression, or partial or complete disappearance of a pre-existing tumor. The definition is meant to include any diminution in the size, potency or growth rate of a pre-existing tumor.

The terms "treatment", "therapeutic use", or "medicinal use" as used herein, shall refer to any and all uses of the claimed compositions which remedy a disease state or symptom, or otherwise prevent, hinder, retard, or reverse the progression of disease or other undesirable symptoms in any way whatsoever.

The term "administered" refers to any method that introduces the cells of the invention (e.g. cancer vaccine) to a mammal. This includes, but is not limited to, intradermal, parenteral, intramuscular, subcutaneous, intraperitoneal, intranasal, intravenous (including via an indwelling catheter), intratumoral, via an afferent lymph vessel, or by another route that is suitable in view of the patient's condition. The compositions of this invention may be administered to the subject at any site. For example, they can be delivered to a site that is "distal" to or "distant" from the primary tumor.

The term "increased immune response" as used herein means that a detectable increase of a specific immune activation is detectable (e.g. an increase in B-cell and/or T-cell response). An example of an increased immune response is an increase in the amount of an antibody that binds an antigen which is not detected or is detected a lower level prior to administration of a cytokine-expressing cellular vaccine of the invention. Another example, is an increased cellular immune response. A cellular immune response involves T cells, and can be observed in vitro (e.g. measured by a Chromium release assay) or in vivo. An increased immune response is typically accompanied by an increase of a specific population of immune cells.

By the term "retarding the growth of a tumor" is meant the slowing of the growth rate of a tumor, the inhibition of an increase in tumor size or tumor cell number, or the reduction in tumor cell number, tumor size, or numbers of tumors.

The term "inhibiting tumor growth" refers to any measurable decrease in tumor mass, tumor volume, amount of tumor cells or growth rate of the tumor. Measurable decreases in tumor mass can be detected by numerous methods known to those skilled in the art. These include direct measurement of accessible tumors, counting of tumor cells (e.g. present in blood), measurements of tumor antigens (e.g. Prostate Specific Antigen (PSA), Alphafetoprotein (AFP) and various visualization techniques (e.g. MRI, CAT-scan and X-rays). Decreases in the tumor growth rate typically correlates with longer survival time for a mammal with cancer.

By the term "therapeutically effective amount" or grammatical equivalents herein refers to an amount of an agent, e.g., a cytokine-expressing cellular vaccine of the invention, that is sufficient to modulate, either by stimulation or suppression, the immune response of an individual. This amount may be different for different individuals, different tumor types, and different preparations. The "therapeutically effective amount" is determined using procedures routinely employed by those of skill in the art such that an "improved therapeutic outcome" results.

As used herein, the terms "improved therapeutic outcome" and "enhanced therapeutic efficacy", relative to cancer refers to a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the patient according to any clinically acceptable criteria, including an increase in life expectancy or an improvement in quality of life (as further described herein)

The term "nucleic acid" refers to deoxyribonucleotides or ribonucleotides and polymers thereof ("polynucleotides") in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985);

Rossolini et al., Mol. Cell. Probes 8: 91-98 (1994)). Nucleotides are indicated by their bases by the following standard abbreviations: adenine (A), cytosine (C), thymine (T), and guanine (G).

Stringent hybridization conditions" and "stringent wash conditions" in the context of nucleic acid hybridization experiments such as Southern and Northern hybridizations are sequence dependent, and are different under different environmental parameters. Longer sequences hybridize at higher temperatures. An extensive guide to the hybridization of nucleic acids is found in Tijssen (1993) Laboratory Techniques in Biochemistry and Molecular Biology-Hybridization with Nucleic Acid Probes part 1 chapter 2 "Overview of principles of hybridization and the strategy of nucleic acid probe assays" Elsevier, N.Y. Generally, highly stringent hybridization and wash conditions are selected to be about 5° C. to 20° C. (preferably 5° C.) lower than the thermal melting point ($T_m$) for the specific sequence at a defined ionic strength and pH. Typically, under highly stringent conditions a probe will hybridize to its target subsequence, but to no other unrelated sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids that have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms described herein or by visual inspection For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J. Mol. Biol. 215: 403-410 (1990), with software that is publicly available through the National Center for Biotechnology Information, or by visual inspection (see generally, Ausubel et al., infra). For purposes of the present invention, optimal alignment of sequences for comparison is most preferably conducted by the local homology algorithm of Smith & Waterman, Adv. Appl. Math. 2: 482 (1981).

As used herein, a "peptide" refers to an amino acid polymer containing between about 8 and about 12 amino acids linked together via peptide bonds. A peptide according to the present invention can comprise additional atoms beyond those of the 8 to twelve amino acids, so long as the peptide retains the ability to bind an MHC I receptor, e.g., an HLA-A2 receptor, and form a ternary complex with the T-cell receptor, the MHC I receptor, and the peptide.

Conservative substitution" refers to the substitution in a polypeptide of an amino acid with a functionally similar amino acid. The following six groups each contain amino acids that are conservative substitutions for one another:

Alanine (A), Serine (S), and Threonine (T)

Aspartic acid (D) and Glutamic acid (E)

Asparagine (N) and Glutamine (Q)

Arginine (R) and Lysine (K)

Isoleucine (I), Leucine (L), Methionine (M), and Valine (V)

Phenylalanine (F), Tyrosine (Y), and Tryptophan (W).

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 48 minutes to 72 minutes. Where the term "about" modifies a value that must be an integer, and 10% above or below the value is not also an integer, the modified value should be rounded to the nearest whole number. For example, "about 12 amino acids" means a range of 11 to 13 amino acids.

The term "physiological conditions," as used herein, refers to the salt concentrations normally observed in human serum. One skilled in the art will recognize that physiological conditions need not mirror the exact proportions of all ions found in human serum, rather, considerable adjustment can be made in the exact concentration of sodium, potassium, calcium, chloride, and other ions, while the overall ionic strength of the solution remains constant.

5.2 FILAMIN-B POLYPEPTIDES AND PEPTIDES DERIVED THEREFROM

In certain aspects as described below, the invention provides methods that comprise assessing cellular immune responses against filamin-B to assess or predict the effectiveness of therapies with genetically altered tumor cells that express cytokines, e.g., GM-CSF. In some embodiments, the therapies are predicted to results in an improved therapeutic outcome for the subject, for example, a reduction in the level of PSA in the patient's serum, a decrease in cancer-associated pain or improvement in the condition of the patient according to any clinically acceptable criteria, including but not limited to a decrease in metastases, an increase in life expectancy or an improvement in quality of life. The filamin-B may be expressed endogenously by cells native to the subject or may be exogenously provided to the subject.

Mammals have three filamin genes, Filamin-A, Filamin-B (beta-filamin; Filamin-3) and Filamin-C. Human filamins are 280-kDa proteins containing an N-terminal actin-binding domain followed by 24 characteristic repeats. They also interact with a number of other cellular proteins. The filamins usually are found as approximately 560-kDA homodimers or heterodimers formed with other filamins. Filamin-B is also known as ABP-278/276 (Xu et al. 1998 Blood 92:1268-1276). See, e.g., Takafuta et al. 1998 J Biol Chem 273:17531-17538; Flier et al., J. Cell Biol., 156(2)361-376, 2002. A 2602 amino acid beta filamin protein sequence may be found at GenBank Accession Nos. NP_001448. The expression patterns of Filamin B and Filamin-A is described for example in Sheen et al., Human Mol. Gen. 11(23) 2845-2854, 2002. Leedman et al., Proc Natl Acad Sci USA. 90(13):5994-8, 1993 describe the cloning of a protein related to actin binding protein, later designated beta filamin.

Accordingly, in certain embodiments, the invention provides an isolated peptide comprising about 8 to about 12 contiguous amino acids of (SEQ ID NO:1), wherein said amino acids bind to HLA-A2 under physiological conditions. Any peptide comprising about 8 to about 12 contiguous amino acids of a filamin polypeptide, preferably a filamin-B polypeptide, wherein said amino acids bind to HLA-A2 under physiological conditions known to one skilled in the art without limitation can be used in connection with the present invention.

In certain embodiments, the peptide comprises about 8 to about 11 amino acids selected from a filamin-B polypeptide (SEQ ID NO:1). In certain embodiments, the peptide comprises about 8 to about 10 amino acids selected from a filamin-B polypeptide (SEQ ID NO:1). In certain embodiments, the peptide comprises about 9 amino acids selected from a filamin-B polypeptide (SEQ ID NO:1).

In certain embodiments, the peptide comprises an amino acid sequence selected from the group consisting of LILGLVWTL (SEQ ID NO:2), GLVEPVNMV (SEQ ID NO:3), GLAPLEVRV (SEQ ID NO:4), SLQESGLKV (SEQ ID NO:5), RLIALLEVL (SEQ ID NO:6), GQGDVMVFV (SEQ ID NO:7), and KLILGLVWT (SEQ ID NO:8).

In certain embodiments, the peptide comprises an amino acid sequence that is LILGLVWTL (SEQ ID NO:2). In certain embodiments, the peptide comprises an amino acid sequence that is GLVEPVNMV (SEQ ID NO:3). In certain embodiments, the peptide comprises an amino acid sequence that is GLAPLEVRV (SEQ ID NO:4). In certain embodiments, the peptide comprises an amino acid sequence that is SLQESGLKV (SEQ ID NO:5). In certain embodiments, the peptide comprises an amino acid sequence that is RLIALLEVL (SEQ ID NO:6). In certain embodiments, the peptide comprises an amino acid sequence that is GQGDVMVFV (SEQ ID NO:7). In certain embodiments, the peptide comprises an amino acid sequence that is KLILGLVWT (SEQ ID NO:8).

In certain embodiments, the peptide is about 12 amino acids long. In certain embodiments, the peptide is about 11 amino acids long. In certain embodiments, the peptide is about 10 amino acids long. In certain embodiments, the peptide is about 9 amino acids long. In certain embodiments, the peptide is about 8 amino acids long.

In certain embodiments, the peptides are selected from the a nucleic acid encoding an antigen associated with a cellular immune response to prostate cancer (e.g., filamin-B) that has a full-length complement that hybridizes to the sequence shown in SEQ ID NO:12 (disclosed as SEQ ID NO:4 in US Patent Publication NO. 2006/0057127, which is hereby incorporated by reference in its entirety) under stringent conditions. The phrase "hybridizing to" refers to the binding, duplexing, or hybridizing of a molecule to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

Thus, a filamin-B peptide associated with a cellular immune response to prostate cancer (e.g., a filamin-B peptide), can be selected from a polypeptide having at least 80, 85, 87, 89, 90, 91, 92, 93, 94, 95, 96, 97, 98, 99% or more % identity over its entire length to the native sequence of filamin-B. For example, a filamin-B coding sequence from which the filamin-B peptides can be selected can have at least 80, 85, 87, 89, 90, 91, 92, 93, 94, 95, 96, 97, 98, 99% or more sequence identity to the sequence presented as SEQ ID NO:1, when compared and aligned for maximum correspondence, as measured a sequence comparison algorithm (as described above) or by visual inspection. In one embodiment, the given % sequence identity exists over a region of the sequences that is at least about amino acids in length. In another embodiment, the given % sequence identity exists over a region of at least about 100 amino acids in length. In another embodiment, the given % sequence identity exists over a region of at least about 150 amino acids in length. In another embodiment, the given % sequence identity exists over the entire length of the sequence.

Conservative substitutions of the peptides are also contemplated. For example, any amino acid of a peptide of the invention can be substituted with a structurally related amino acid as described herein. Preferably, the peptides having conservative substitutions retain the ability to bind class I MHC molecules, e.g., HLA-A2 molecules, and/or stimulate CTL activity when presented by an appropriate cell.

5.3 METHODS OF USING FILAMIN-B PEPTIDES

In accordance with the present invention, the peptides of the invention find use in a variety of methods, including methods for determining whether a cellular immune response against cancer cells has been induced in a subject, methods for determining whether a cellular immune response effective to treat, prevent, or ameliorate a symptom of prostate cancer in a subject has been induced in the subject, methods for determining whether a subject afflicted with prostate cancer is likely to respond to treatment with genetically modified tumor cells that produce GM-CSF, methods for generating CTLs that are activated by cells expressing HLA-A2 class T MHC having a peptide comprising about 8 to about 12 amino acids selected from a filamin-B polypeptide (SEQ ID NO:1) bound thereto, and methods for assessing the effectiveness of prostate cancer therapy with genetically modified tumor cells that express GM-CSF to treat or ameliorate a symptom of prostate cancer of a subject in need thereof.

Accordingly, in certain embodiments, the invention provides a method for determining whether a cellular immune response against cancer cells has been induced in a subject, comprising: contacting cytotoxic T lymphocytes (CTLs) from the subject to cells that express an HLA-A2 class I MHC receptor, wherein the HLA-A2 receptor has a peptide comprising about 8 to about 12 amino acids selected from a filamin-B polypeptide (SEQ ID NO:1) bound thereto; and detecting activation of the CTLs by the cells that express the HLA-A2 receptor, wherein detecting said activation indicates that a cellular immune response against prostate cancer cells has been induced in the subject.

In certain embodiments, the peptide comprises about 8 to about 11 amino acids selected from a filamin-B polypeptide (SEQ ID NO:1). In certain embodiments, the peptide comprises about 8 to about 10 amino acids selected from a filamin-B polypeptide (SEQ ID NO:1). In certain embodiments, the peptide comprises about 9 amino acids selected from a filamin-B polypeptide (SEQ ID NO:1).

In certain embodiments, the peptide comprises an amino acid sequence selected from the group consisting of LILGLVWTL (SEQ ID NO:2), GLVEPVNMV (SEQ ID NO:3), GLAPLEVRV (SEQ ID NO:4), SLQESGLKV (SEQ ID NO:5), RLIALLEVL (SEQ ID NO:6), GQGDVMVFV (SEQ ID NO:7), and KLILGLVWT (SEQ ID NO:8).

In certain embodiments, the peptide comprises an amino acid sequence that is LILGLVWTL (SEQ ID NO:2). In certain embodiments, the peptide comprises an amino acid sequence that is GLVEPVNMV (SEQ ID NO:3). In certain embodiments, the peptide comprises an amino acid sequence that is GLAPLEVRV (SEQ ID NO:4). In certain embodiments, the peptide comprises an amino acid sequence that is SLQESGLKV (SEQ ID NO:5). In certain embodiments, the peptide comprises an amino acid sequence that is RLIALLEVL (SEQ ID NO:6). In certain embodiments, the peptide comprises an amino acid sequence that is GQGDVMVFV (SEQ ID NO:7). In certain embodiments, the peptide comprises an amino acid sequence that is KLILGLVWT (SEQ ID NO:8).

In certain embodiments, the cells that express the HLA-A2 receptor are primate cells, canine cells, rodent cells, lagomorph cells, bovine cells, insect cells, or equine cells. In certain embodiments, the cells that express the HLA-A2 receptor are human cells, mouse cells, rat cells, or hamster cells. In certain embodiments, the cells that express the HLA-A2 receptor are human cells.

In certain embodiments, the cells that express the HLA-A2 receptor are from an immortalized cell line. In certain embodiments, the cells that express the HLA-A2 receptor are T2 cells.

In certain embodiments, activation of the CTLs is detected by detecting secretion of IFN-γ by the CTLs. In certain embodiments, activation of the CTLs is detected by detecting proliferation of the CTLs. In certain embodiments, activation of the CTLs is detected by detecting lysis of the cells expressing the HLA-A2 receptor by the CTLs.

In certain embodiments, the cancer cells are prostate cancer cells.

In another aspect, the invention provides a method for determining whether a cellular immune response effective to treat, prevent, or ameliorate a symptom of prostate cancer in a subject has been induced in the subject, comprising: contacting in vitro CTLs from the subject to cells that express an HLA-A2 class I MHC receptor, wherein the HLA-A2 receptor has a peptide comprising about 8 to about 12 amino acids selected from a filamin-B polypeptide (SEQ ID NO:1) bound thereto; and detecting activation of the CTLs by the cells that express the HLA-A2 receptor, wherein detecting said activation indicates that a cellular immune response effective to treat, prevent, or ameliorate a symptom of prostate cancer has been induced in the subject.

In certain embodiments, the peptide comprises an amino acid sequence selected from the group consisting of LILGLVWTL (SEQ ID NO:2), GLVEPVNMV (SEQ ID NO:3), GLAPLEVRV (SEQ ID NO:4), SLQESGLKV (SEQ ID NO:5), RLIALLEVL (SEQ ID NO:6), GQGDVMVFV (SEQ ID NO:7), and KLILGLVWT (SEQ ID NO:8).

In certain embodiments, the immune response that has been induced is effective to prevent prostate cancer in the subject. In certain embodiments, the immune response that has been induced is effective to treat prostate cancer in the subject. In certain embodiments, the immune response that has been induced is effective to ameliorate a symptom of prostate cancer in the subject. In certain embodiments, the symptom of prostate cancer that is ameliorated is selected from the group consisting of a reduction in the level of prostate specific antigen (PSA) level in the subject's serum, cancer-associated pain, and metastasis.

In certain embodiments, activation of the CTLs is detected by detecting secretion of IFN-γ by the CTLs. In certain embodiments, activation of the CTLs is detected by detecting proliferation of the CTLs. In certain embodiments, activation of the CTLs is detected by detecting lysis of the cells expressing the HLA-A2 receptor by the CTLs.

In still another aspect, the invention provides a method for detail lining whether a subject afflicted with prostate cancer is likely to respond to treatment with genetically modified tumor cells that produce GM-CSF, comprising: contacting CTLs from the subject to cells that express an HLA-A2 class I MHC receptor, wherein the HLA-A2 receptor has a peptide comprising about 8 to about 12 amino acids selected from a filamin-B polypeptide (SEQ ID NO:1) bound thereto; and detecting activation of the CTLs by the cells that express the HLA-A2 receptor, wherein detecting said activation indicates that subject afflicted with prostate cancer is likely to respond to treatment with genetically modified tumor cells that produce GM-CSF.

In certain embodiments, the peptide comprises an amino acid sequence selected from the group consisting of LILGLVWTL (SEQ ID NO:2), GLVEPVNMV (SEQ ID NO:3), GLAPLEVRV (SEQ ID NO:4), SLQESGLKV (SEQ ID NO:5), RLIALLEVL (SEQ ID NO:6), GQGDVMVFV (SEQ ID NO:7), and KLILGLVWT (SEQ ID NO:8).

In certain embodiments, activation of the CTLs is detected by detecting secretion of IFN-γ by the CTLs. In certain embodiments, activation of the CTLs is detected by detecting proliferation of the CTLs. In certain embodiments, activation of the CTLs is detected by detecting lysis of the cells expressing the HLA-A2 receptor by the CTLs.

In yet another aspect, the invention provides a method for generating CTLs that are activated by cells expressing HLA-A2 class I MHC having a peptide comprising about 8 to about 12 amino acids selected from a filamin-B polypeptide (SEQ ID NO:1) bound thereto, comprising: contacting a population of CTLs with cells expressing HLA-A2 class I MHC having a peptide comprising about 8 to about 12 amino acids selected from a filamin-B polypeptide (SEQ ID NO:1) bound thereto; identifying one or more CTLs from the population that are activated by the contact of step (a); and isolating said one or more CTLs.

In certain embodiments, activation of the CTLs is detected by detecting secretion of IFN-γ by the CTLs. In certain embodiments, activation of the CTLs is detected by detecting proliferation of the CTLs. In certain embodiments, activation of the CTLs is detected by detecting lysis of the cells expressing the HLA-A2 receptor by the CTLs.

In certain embodiments, the method further comprises clonally expanding said one or more CTLs. In certain embodiments, the method further comprises administering said one or more CTLs to a subject afflicted with prostate cancer.

In certain embodiments, genetically modified tumor cells expressing GM-CSF have also been administered to said subject. In certain embodiments, genetically modified tumor cells expressing GM-CSF are administered to said subject concurrently with said CTLs.

In still another aspect, the invention provides a method for assessing the effectiveness of prostate cancer therapy with genetically modified tumor cells that express GM-CSF to treat or ameliorate a symptom of prostate cancer of a subject in need thereof, comprising administering genetically modified tumor cells that express GM-CSF to the subject; isolating CTLs from the subject; and determining whether the CTLs are activated by contacting cells that express the HLA-A2 receptor class I MHC having a peptide comprising about 8 to about 12 amino acids selected from a filamin-B polypeptide (SEQ ID NO:1) bound thereto, wherein activation indicates that the treatment with genetically modified tumor cells that produce GM-CSF is effective to treat or ameliorate a symptom of prostate cancer in said subject.

In certain embodiments, the peptide comprises an amino acid sequence selected from the group consisting of LILGLVWTL (SEQ ID NO:2), GLVEPVNMV (SEQ ID NO:3), GLAPLEVRV (SEQ ID NO:4), SLQESGLKV (SEQ ID NO:5), RLIALLEVL (SEQ ID NO:6), GQGDVMVFV (SEQ ID NO:7), and KLILGLVWT (SEQ ID NO:8).

In certain embodiments, activation of the CTLs is detected by detecting secretion of IFN-γ by the CTLs. In certain embodiments, activation of the CTLs is detected by detecting proliferation of the CTLs. In certain embodiments, activation of the CTLs is detected by detecting lysis of the cells expressing the HLA-A2 receptor by the CTLs.

In certain embodiments, the treatment with genetically modified tumor cells that produce GM-CSF is effective to treat prostate cancer in the subject. In certain embodiments, the treatment with genetically modified tumor cells that produce GM-CSF is effective to ameliorate a symptom of prostate cancer in the subject. In certain embodiments, the symptom of prostate cancer that is ameliorated is selected from the group consisting of a reduction in the level of prostate specific antigen (PSA) level in the subject's serum, cancer-associated pain, and metastasis.

5.4 KITS

In still another aspect, the invention provides kits comprising a peptide of the invention. Accordingly, in certain embodiments, the invention provides a kit, comprising a first container containing a peptide comprising about 8 to about 12 amino acids selected from a filamin-B polypeptide (SEQ ID NO:1), wherein said peptide binds to HLA-A2, and a second container containing cells expressing HLA-A2 class I MHC.

In certain embodiments, the peptide comprises an amino acid sequence selected from the group consisting of LILGLVWTL (SEQ ID NO:2), GLVEPVNMV (SEQ ID NO:3), GLAPLEVRV (SEQ ID NO:4), SLQESGLKV (SEQ ID NO:5), RLIALLEVL (SEQ ID NO:6), GQGDVMVFV (SEQ ID NO:7), and KLILGLVWT (SEQ ID NO:8).

In certain embodiments, the peptide comprises an amino acid sequence that is LILGLVWTL (SEQ ID NO:2). In certain embodiments, the peptide comprises an amino acid sequence that is GLVEPVNMV (SEQ ID NO:3). In certain embodiments, the peptide comprises an amino acid sequence that is GLAPLEVRV (SEQ ID NO:4). In certain embodiments, the peptide comprises an amino acid sequence that is SLQESGLKV (SEQ ID NO:5). In certain embodiments, the peptide comprises an amino acid sequence that is RLIALLEVL (SEQ ID NO:6). In certain embodiments, the peptide comprises an amino acid sequence that is GQGDVMVFV (SEQ ID NO:7). In certain embodiments, the peptide comprises an amino acid sequence that is KLILGLVWT (SEQ ID NO:8).

In certain embodiments, the kit further comprises instructions for use of the kit to determine whether a cellular immune response against prostate cancer cells has been induced in a subject. In certain embodiments, the kit further comprises instructions for use of the kit to determine whether a cellular immune response effective to treat, prevent, or ameliorate prostate cancer in a subject has been induced in the subject. In certain embodiments, the kit further comprises instructions for use of the kit to determine whether a subject afflicted with prostate cancer is likely to respond to treatment with genetically modified tumor cells that produce GM-CSF. In certain embodiments, the kit further comprises a container containing genetically modified tumor cells that express GM-CSF.

In certain embodiments, the kit further comprises instructions directing administration of the genetically modified tumor cells to a subject in need thereof.

5.5 IMMUNOGENIC COMPOSITIONS COMPRISING CELLS EXPRESSING CYTOKINES

The present invention relates, in part, to methods relating to the effectiveness of cancer therapy with cells genetically altered to express cytokines, e.g., GM-CSF. Cancer therapies with cells genetically altered to express cytokines are extensively described hereinafter.

In one aspect, the method of treating prostate cancer in a subject comprises administering genetically modified cytokine-expressing cells to the subject as part of a therapeutic treatment for cancer. The method can be carried out by genetically modifying (transducing) a first population of tumor cells to produce a cytokine, e.g., GM-CSF, and administering the first population of tumor cells alone or in combination with a second population of tumor cells to the subject. The tumor cells may be tumor cells from the same individual (autologous), from a different individual (allogeneic) or bystander cells (further described below). Typically, the tumor cells are from a tumor cell line of the same type as the tumor or cancer being treated, e.g., the modified cells are prostate or prostate cancer cells and the patient has prostate cancer.

Typically the genetically modified tumor cells are rendered proliferation incompetent prior to administration. In one embodiment, the mammal is a human who harbors prostate tumor cells of the same type as the genetically modified cytokine-expressing tumor cells. In a preferred embodiment, an improved therapeutic outcome is evident following administration of the genetically modified cytokine-expressing tumor cells to the subject. Any of the various parameters of an improved therapeutic outcome for a prostate cancer patient known to those of skill in the art may be used to assess the efficacy of genetically modified cytokine-expressing tumor cell therapy, e.g., a reduction in the serum level of PSA.

In still another aspect, the method is effective to stimulate a systemic immune response in a prostate cancer patient, comprising administering a therapeutically effective amount of proliferation incompetent genetically modified cytokine-expressing cells to the subject. The systemic immune response to the tumor may result in tumor regression or inhibit the growth of the tumor. In some embodiments, the prostate cancer is metastatic prostate cancer. In some embodiments, the prostate cancer is refractory to hormone therapy. In some embodiments, the primary prostate tumor has been treated, e.g., by ablation or recission and metasteses of the primary prostate cancer are treated by immunotherapy as described herein.

In one preferred embodiment, a viral or nonviral vector is utilized to deliver a human GM-CSF transgene (coding sequence) to a human tumor cell ex vivo. After transduction, the cells are irradiated to render them proliferation incompetent. The proliferation incompetent GM-CSF expressing tumor cells are then re-administered to the patient (e.g., by the intradermal or subcutaneous route) and thereby function as a cancer vaccine. The human tumor cell may be a primary tumor cell or derived from a tumor cell line.

In general, the genetically modified tumor cells include one or more of autologous tumor cells, allogeneic tumor cells and tumor cell lines (i.e., bystander cells). The tumor cells may be transduced in vitro, ex vivo or in vivo. Autologous and allogeneic cancer cells that have been genetically modified to express a cytokine, e.g., GM-CSF, followed by readministration to a patient for the treatment of cancer are described in U.S. Pat. Nos. 5,637,483, 5,904,920 and 6,350,445, expressly incorporated by reference herein. A form of GM-CSF-expressing genetically modified tumor cells or a "cytokine-expressing cellular vaccine" ("GVAX"®), for the treatment of pancreatic cancer is described in U.S. Pat. Nos. 6,033,674 and 5,985,290, expressly incorporated by reference herein. A universal immunomodulatory genetically modified bystander cell line is described in U.S. Pat. No. 6,464,973, expressly incorporated by reference herein.

An allogeneic form of GVAX® wherein the cellular vaccine comprises one or more prostate tumor cell lines selected from the group consisting of DU145, PC-3, and LNCaP is described in WO/0026676, expressly incorporated by reference herein. LNCaP is a PSA-producing prostate tumor cell line, while PC-3 and DU-145 are non-PSA-producing prostate tumor cell lines (Pang S. et al., Hum Gene Ther. 1995 November; 6(11):1417-1426).

Clinical trials employing GM-CSF-expressing cellular vaccines (GVAX®) have been undertaken for treatment of prostate cancer, melanoma, lung cancer, pancreatic cancer, renal cancer, and multiple myeloma. A number of clinical trials using GVAX® cellular vaccines have been described, most notably in melanoma, and prostate, renal and pancreatic carcinoma (Simons J W et al. Cancer Res. 1999; 59:5160-5168; Simons J W et al. Cancer Res 1997; 57:1537-1546; Soiffer R et al. Proc. Natl. Acad. Sci. USA 1998; 95:13141-13146; Jaffee, et al. J Clin Oncol 2001; 19:145-156; Salgia et al. J Clin Oncol 2003 21:624-30; Soiffer et al. J Clin Oncol 2003 21:3343-50; Nemunaitis et al. J Natl Cancer Inst. 2004 Feb. 18 96(4):326-31).

By way of example, in one approach, genetically modified GM-CSF expressing tumor cells are provided as an allogeneic or bystander cell line and one or more additional cancer therapeutic agents is included in the treatment regimen. In another approach, one or more additional transgenes are expressed by an allogeneic or bystander cell line while a cytokine (i.e., GM-CSF) is expressed by autologous or allogeneic cells. The GM-CSF coding sequence is introduced into the tumor cells using a viral or non-viral vector and routine methods commonly employed by those of skill in the art. The preferred coding sequence for GM-CSF is the genomic sequence described in Huebner K. et al., Science 230(4731):1282-5, 1985, however, in some cases the cDNA form of GM-CSF finds utility in practicing the methods (Cantrell et al., Proc. Natl. Acad. Sci., 82, 6250-6254, 1985).

The genetically modified tumor cells can be cryopreserved prior to administration. Preferably, the genetically modified tumor cells are irradiated at a dose of from about 50 to about 200 rads/min, even more preferably, from about 120 to about 140 rads/min prior to administration to the patient. Preferably, the cells are irradiated with a total dose sufficient to inhibit substantially 100% of the cells from further proliferation. Thus, desirably the cells are irradiated with a total dose of from about 10,000 to 20,000 rads, optimally, with about 15,000 rads. Typically more than one administration of cytokine (e.g., GM-CSF) producing cells is delivered to the subject in a course of treatment. Dependent upon the particular course of treatment, multiple injections may be given at a single time point with the treatment repeated at various time intervals. For example, an initial or "priming" treatment may be followed by one or more "booster" treatments. Such "priming" and "booster" treatments are typically delivered by the same route of administration and/or at about the same site. When multiple doses are administered, the first immunization dose may be higher than subsequent immunization doses. For example, a $5 \times 10^6$ prime dose may be followed by several booster doses of $10^6$ to $3 \times 10^6$ GM-CSF producing cells.

A single injection of cytokine-producing cells is typically between about $10^6$ to $10^8$ cells, e.g., $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $10^7$, $2 \times 10^7$, $5 \times 10^7$ or as many as $10^8$ cells. In one embodiment, there are between $10^6$ and $10^8$ cytokine-producing cells per unit dose. The number of cytokine-producing cells may be adjusted according, for example, to the level of cytokine produced by a given cytokine producing cellular vaccine.

In some embodiments, cytokine-producing cells are administered in a dose that is capable of producing at least 500 ng of GM-CSF per 24 hours per one million cells. Determination of optimal cell dosage and ratios is a matter of routine determination and within the skill of a practitioner of ordinary skill, in light of the disclosure provided herein.

In treating a prostate cancer patient according to the methods described herein, the attending physician may administer lower doses of the cytokine-expressing tumor cell vaccine and observe the patient's response. Larger doses of the cytokine-expressing tumor cell vaccine may be administered until the an improved therapeutic outcome is evident.

Cytokine-producing cells of the invention are processed to remove most additional components used in preparing the cells. In particular, fetal calf serum, bovine serum components, or other biological supplements in the culture medium are removed. In one embodiment, the cells are washed, such as by repeated gentle centrifugation, into a suitable pharmacologically compatible excipient. Compatible excipients include various cell culture media, isotonic saline, with or without a physiologically compatible buffer, for example, phosphate or hepes, and nutrients such as dextrose, physiologically compatible ions, or amino acids, particularly those devoid of other immunogenic components. Carrying reagents, such as albumin and blood plasma fractions and inactive thickening agents, may also be used.

5.5.1. Autologous Cells

The use of autologous genetically modified GM-CSF expressing cells provides advantages since each patient's tumor expresses a unique set of tumor antigens that can differ from those found on histologically-similar, MHC-matched tumor cells from another patient. See, e.g., Kawakami et al., J. Immunol., 148, 638-643 (1992); Darrow et al., J. Immunol., 142, 3329-3335 (1989); and Hom et al., J. Immunother., 10, 153-164 (1991). In contrast, MHC-matched tumor cells provide the advantage that the patient need not be taken to surgery to obtain a sample of their tumor for genetically modified tumor cell production.

In one preferred aspect, the method of treating prostate cancer comprises: (a) obtaining tumor cells from a mammalian subject harboring a prostate tumor; (b) genetically modifying the tumor cells to render them capable of producing an increased level of GM-CSF relative to unmodified tumor cells; (c) rendering the modified tumor cells proliferation incompetent; and (d) readministering the genetically modified tumor cells to the mammalian subject from which the tumor cells were obtained or to a mammal with the same MHC type as the mammal from which the tumor cells were obtained. The administered tumor cells are autologous and MHC-matched to the host. Preferably, the composition is administered intradermally, subcutaneously or intratumorally to the mammalian subject.

In some cases, a single autologous tumor cell may express GM-CSF alone or GM-CSF plus one or more additional transgenes. In other cases, GM-CSF and the one or more additional transgenes may be expressed by different autologous tumor cells. In one aspect of the invention, an autologous tumor cell is modified by introduction of a vector comprising a nucleic acid sequence encoding GM-CSF, operatively linked to a promoter and expression/control sequences necessary for expression thereof. In another aspect, the same autologous tumor cell or a second autologous tumor cell can be modified by introduction of a vector comprising a nucleic acid sequence encoding at least one additional transgene operatively linked to a promoter and expression/control sequences necessary for expression thereof. The nucleic acid sequence encoding the one or more transgenes can be introduced into the same or a different autologous tumor cell using the same or a different vector. The nucleic acid sequence encoding the transgene(s) may or may not further comprise a selectable marker sequence operatively linked to a promoter. Desirably, the autologous tumor cell expresses high levels of GM-CSF.

5.5.2. Allogeneic Cells

Researchers have sought alternatives to autologous and MHC-matched cells as tumor vaccines, as reviewed by Jaffee et al., Seminars in Oncology, 22, 81-91 (1995). Early tumor vaccine strategies were based on the understanding that the vaccinating cells function as the antigen presenting cells (APCs) that present tumor antigens on their MHC class I and II molecules, and directly activate the T cell arm of the immune system. The results of Huang et al. (Science, 264, 961-965, 1994), indicate that professional APCs of the host rather than the vaccinating cells prime the T cell arm of the immune system by secreting cytokine(s) such as GM-CSF such that bone marrow-derived APCs are recruited to the region of the tumor. The bone marrow-derived APCs take up the whole cellular protein of the tumor for processing, and then present the antigenic peptide(s) on their MHC class I and II molecules, thereby priming both the CD4+ and the CD8+ T cell arms of the immune system, resulting in a systemic tumor-specific anti-tumor immune response. Without being bound by theory, these results suggest that it may not be necessary or optimal to use autologous or MHC-matched cells in order to elicit an anti-cancer immune response and that the transfer of allogeneic MHC genes (from a genetically dissimilar individual of the same species) can enhance tumor immunogenicity. More specifically, in certain cases, the rejection of tumors expressing allogeneic MHC class I molecules has resulted in enhanced systemic immune responses against subsequent challenge with the unmodified parental tumor. See, e.g., Jaffee et al., supra, and Huang et al., supra.

As used herein, a "tumor cell line" comprises cells that were initially derived from a tumor. Such cells typically exhibit indefinite growth in culture. In one aspect, the method for treating prostate cancer comprises: (a) obtaining a tumor cell line; (b) genetically modifying the tumor cell line to render the cells capable of producing an increased level of a cytokine, e.g., GM-CSF, relative to the unmodified tumor cell line; (c) rendering the modified tumor cell line proliferation incompetent; and (d) administering the tumor cell line to a mammalian subject (host) having at least one tumor that is of the same type of tumor as that from which the tumor cell line was obtained. In some embodiments, the administered tumor cell line is allogeneic and is not MHC-matched to the host. Such allogeneic lines provide the advantage that they can be prepared in advance, characterized, aliquoted in vials containing known numbers of transgene (e.g., GM-CSF) expressing cells and stored (i.e. frozen) such that well characterized cells are available for administration to the patient. Methods for the production of genetically modified allogeneic cells are described for example in WO 00/72686, expressly incorporated by reference herein.

In one approach to preparing genetically modified GM-CSF expressing allogeneic cells, a nucleic acid sequence (transgene) encoding GM-CSF alone or in combination with the nucleic acid coding sequence for one or more additional transgenes is introduced into a cell line that is an allogeneic tumor cell line (i.e., derived from an individual other than the individual being treated). In another approach, a nucleic acid sequence (transgene) encoding GM-CSF alone or in combination with the nucleic acid coding sequence for one or more additional transgenes is introduced into separate allogeneic tumor cell lines. In yet another approach two or more different genetically modified allogeneic GM-CSF expressing cell lines (e.g. LNCAP and PC-3) are administered in combination, typically at a ratio of 1:1. In general, the cell or population of cells is from a tumor cell line of the same type as the tumor or cancer being treated, e.g. prostate cancer. The nucleic acid sequence encoding the transgene(s) may be introduced into the same or a different allogeneic tumor cell using the same or a different vector. The nucleic acid sequence encoding the transgene(s) may or may not further comprise a selectable marker sequence operatively linked to a promoter. Desirably, the allogeneic cell line expresses high levels of GM-CSF.

In another aspect, one or more genetically modified GM-CSF expressing allogeneic cell lines can be exposed to an antigen, such that the patient's immune response to the antigen is increased in the presence of GM-CSF, e.g., an allogeneic or bystander cell that has been genetically modified to express GM-CSF. Such exposure may take place ex vivo or in vivo. In one preferred embodiment, the antigen is a peptide comprising an amino acid sequence obtained from filamin-B, as described extensively above. The filamin-B peptide can be provided by (on) cells that are administered to the subject or may be provided by cells native to the patient. In such cases, the composition can be rendered proliferation-incompetent, typically by irradiation, wherein the allogeneic cells are plated in a tissue culture plate and irradiated at room temperature using a Cs source, as further described herein. An allogeneic cellular vaccine composition of the invention may comprise allogeneic cells plus other cells, i.e. a different type of allogeneic cell, an autologous cell, or a bystander cell that may or may not be genetically modified. If genetically modified, the different type of allogeneic cell, autologous cell, or bystander cell may express GM-CSF or another transgene. The ratio of allogeneic cells to other cells in a given administration will vary dependent upon the combination.

Any suitable route of administration can be used to introduce an allogeneic cell line composition into the patient, preferably, the composition is administered intradermally, subcutaneously or intratumorally.

The use of allogeneic cell lines in practicing the present invention provides the therapeutic advantage that administration of a genetically modified GM-CSF expressing cell line to a patient with cancer, together with an autologous cancer antigen, paracrine production of GM-CSF results in an effective immune response to a tumor. This obviates the need to culture and transduce autologous tumor cells for each patient.

5.5.3. Bystander Cells

In one further aspect, a universal immunomodulatory genetically modified transgene-expressing bystander cell that expresses at least one transgene can be used in the immunotherapies described herein. The same universal bystander cell line may express more than one transgene or individual transgenes may be expressed by different universal bystander cell lines. The universal bystander cell line comprises cells which either naturally lack major histocompatibility class I (MHC-I) antigens and major histocompatibility class II (MHC-II) antigens or have been modified so that they lack MHC-I antigens and MHC-II antigens. In one aspect, a universal bystander cell line can be modified by introduction of a vector wherein the vector comprises a nucleic acid sequence encoding a transgene, e.g., a cytokine such as GM-CSF, operably linked to a promoter and expression control sequences necessary for expression thereof. In another aspect, the same universal bystander cell line or a second a universal bystander cell line is modified by introduction of a vector comprising a nucleic acid sequence encoding at least one additional transgene operatively linked to a promoter and expression control sequences necessary for expression thereof. The nucleic acid sequence encoding the transgene(s) may be introduced into the same or a different universal bystander cell line using the same or a different vector. The nucleic acid sequence encoding the transgene(s) may or may not further comprise a selectable marker sequence operatively linked to a promoter. Any combination of transgene(s) that stimulate an anti-tumor immune response can be used. The universal bystander cell line preferably grows in defined, i.e., serum-free medium, preferably as a suspension.

An example of a preferred universal bystander cell line is K562 (ATCC CCL-243; Lozzio et al., Blood 45(3): 321-334 (1975); Klein et al., Int. J. Cancer 18: 421-431 (1976)). A detailed description of the generation of human bystander cell lines is described for example in U.S. Pat. No. 6,464,973, expressly incorporated by reference herein.

Desirably, the universal bystander cell line expresses high levels of the transgene, e.g. a cytokine such as GM-CSF.

In the methods, the one or more universal bystander cell lines can be incubated with an autologous cancer antigen, e.g., provided by an autologous tumor cell (which together comprise a universal bystander cell line composition), then the universal bystander cell line composition can be administered to the patient. Any suitable route of administration can be used to introduce a universal bystander cell line composition into the patient. Preferably, the composition is administered intradermally, subcutaneously or intratumorally.

Typically, the autologous cancer antigen can be provided by a cell of the cancer to be treated, i.e., an autologous cancer cell. In such cases, the composition is rendered proliferation-incompetent by irradiation, wherein the bystander cells and cancer cells are plated in a tissue culture plate and irradiated at room temperature using a Cs source, as detailed above.

The ratio of bystander cells to autologous cancer cells in a given administration will vary dependent upon the combination. With respect to GM-CSF-producing bystander cells, the ratio of bystander cells to autologous cancer cells in a given administration should be such that a therapeutically effective level of GM-CSF is produced. In addition to the GM-CSF threshold, the ratio of bystander cells to autologous cancer cells should not be greater than 1:1. Appropriate ratios of bystander cells to tumor cells or tumor antigens can be determined using routine methods known in the art.

The use of bystander cell lines in practicing the present invention provides the therapeutic advantage that, through administration of a cytokine-expressing bystander cell line and at least one additional cancer therapeutic agent (expressed by the same or a different cell) to a patient with cancer, together with an autologous cancer antigen, paracrine production of an immunomodulatory cytokine, results in an effective immune response to a tumor. This obviates the need to culture and transduce autologous tumor cells for each patient.

Typically a minimum dose of about 3500 rads is sufficient to inactivate a cell and render it proliferation-incompetent, although doses up to about 30,000 rads are acceptable. In some embodiment, the cells are irradiated at a dose of from about 50 to about 200 rads/min or from about 120 to about 140 rads/min prior to administration to the mammal. Typically, when using irradiation, the levels required are 2,500 rads, 5,000 rads, 10,000 rads, 15,000 rads or 20,000 rads. In one embodiment, a dose of about 10,000 rads is used to inactivate a cell and render it proliferation-incompetent. It is understood that irradiation is but one way to render cells proliferation-incompetent, and that other methods of inactivation which result in cells incapable of multiple rounds of cell division but that retain the ability to express transgenes (e.g. cytokines) are included in the present invention (e.g., treatment with mitomycin C, cycloheximide, and conceptually analogous agents, or incorporation of a suicide gene by the cell).

5.5.4. Cytokines

A "cytokine" or grammatical equivalent, includes, without limitation, those hormones that act locally and do not circulate in the blood, and which, when used in accordance with the present invention, will result in an alteration of an individual's immune response. Also included in the definition of cytokine are adhesion or accessory molecules which result in an alteration of an individual's immune response. Thus, examples of cytokines include, but are not limited to, IL-1 (a or P), IL-2, IL-3, IL-4, IL-5, IL-6, IL-7, IL-8, IL-9, IL-10, IL-11, IL-12, GM-CSF, M-CSF, G-CSF, LIF, LT, TGF-β, γ-IFN, a-EFN, P-IFN, TNF-α, BCGF, CD2, or ICAM. Descriptions of the aforementioned cytokines as well as other applicable immunomodulatory agents may be found in "Cytokines and Cytokine Receptors," A. S. Hamblin, D. Male (ed.), Oxford University Press, New York, N.Y. (1993)), or the "Guidebook to Cytokines and Their Receptors," N. A. Nicola (ed.), Oxford University Press, New York, N.Y. (1995)). Where therapeutic use in humans is contemplated, the cytokines will preferably be substantially similar to the human form of the protein or will have been derived from human sequences (i.e., of human origin). In one preferred embodiment, the transgene is a cytokine, such as GM-CSF.

Additionally, cytokines of other mammals with substantial structural homology and/or amino acid sequence identity to the human forms of a given cytokine, will be useful when demonstrated to exhibit similar activity on the human immune system. Similarly, proteins that are substantially analogous to any particular cytokine, but have conservative changes of protein sequence, can also be used. Thus, conservative substitutions in protein sequence may be possible without disturbing the functional abilities of the protein molecule, and thus proteins can be made that function as cytokines in the present invention but have amino acid sequences that differ slightly from currently known sequences. Such conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Granulocyte-macrophage colony stimulating factor (GM-CSF) is a cytokine produced by fibroblasts, endothelial cells, T cells and macrophages. This cytokine has been shown to induce the growth of hematopoetic cells of granulocyte and macrophage lineages. In addition, it also activates the antigen processing and presenting function of dendritic cells, which are the major antigen presenting cells (APC) of the immune system. Results from animal model experiments have convincingly shown that GM-CSF producing cells (i.e. GVAX®) are able to induce an immune response against parental, non-transduced cells.

GM-CSF augments the antigen presentation capability of the subclass of dendritic cells (DC) capable of stimulating robust anti-tumor responses (Gasson et al. Blood 1991 Mar. 15; 77(6):1131-45; Mach et al. Cancer Res. 2000 Jun. 15; 60(12):3239-46; reviewed in Mach and Dranoff, Curr Opin Immunol. 2000 October; 12(5):571-5). See, e.g., Boon and Old, Curr Opin Immunol. 1997 Oct. 1; 9(5):681-3). Presentation of tumor antigen epitopes to T cells in the draining lymph nodes is expected to result in systemic immune responses to tumor metastases. Also, irradiated tumor cells expressing GM-CSF have been shown to function as potent vaccines against tumor challenge (as further described in the section below, entitled "GVAX®"). Localized high concentrations of certain cytokines, delivered by genetically modified cells, have been found to lead to tumor regression (Abe et al., J. Canc. Res. Clin. Oncol. 121: 587-592 (1995); Gansbacher et al., Cancer Res. 50: 7820-7825 (1990); Formi et al., Cancer and Met. Reviews 7: 289-309 (1988). PCT publication WO200072686 describes tumor cells expressing various cytokines.

In one embodiment, the cellular immunogenic composition comprises a GM-CSF coding sequence operatively linked to regulatory elements for expression in the cells of the vaccine. The GM-CSF coding sequence may code for a murine or human GM-CSF and may be in the form of genomic DNA (SEQ ID NO:9; disclosed as SEQ ID NO:1 in US Patent Publication NO. 2006/0057127, which is hereby incorporated by reference in its entirety) or cDNA (SEQ ID NO:10; disclosed as SEQ ID NO:2 in US Patent Publication NO. 2006/0057127, which is hereby incorporated by reference in its entirety). In the case of cDNA, the coding sequence for GM-CSF does not contain intronic sequences to be spliced out prior to translation. In contrast, for genomic GM-CSF, the coding sequence contains at least one native GM-CSF intron that is spliced out prior to translation. In one embodiment, the GM-CSF coding sequence encodes the amino acid sequence presented as SEQ ID NO:11 (disclosed as SEQ ID NO:3 in US Patent Publication NO. 2006/0057127, which is hereby incorporated by reference in its entirety). Other examples of GM-CSF coding sequences are found in Genbank accession numbers: AF373868, AC034228, AC034216, M 10663 and NM000758.

A GM-CSF coding sequence can be a full-length complement that hybridizes to the sequence shown in SEQ ID NO:9 or SEQ ID NO:10 under stringent conditions. The phrase "hybridizing to" refers to the binding, duplexing, or hybridizing of a molecule to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

It therefore follows that the coding sequence for a cytokine such as GM-CSF, can have at least 80, 85, 87, 89, 90, 91, 92, 93, 94, 95, 96, 97, 98, 99% or more % identity over its entire length to a native GM-CSF coding sequence. For example, a GM-CSF coding sequence can have at least 80, 85, 87, 89, 90, 91, 92, 93, 94, 95, 96, 97, 98, 99% or more sequence identity to a sequence presented as SEQ ID NO:9 or SEQ ID NO:10, when compared and aligned for maximum correspondence, as measured a sequence comparison algorithm (as described above) or by visual inspection. In one embodiment, the given % sequence identity exists over a region of the sequences that is at least about 50 nucleotides in length. In another embodiment, the given % sequence identity exists over a region of at least about 100 nucleotides in length. In another embodiment, the given % sequence identity exists over a region of at least about 200 nucleotides in length. In another embodiment, the given % sequence identity exists over the entire length of the sequence. Preferably, the GM-CSF has authentic GM-CSF activity, e.g., can bind the GM-CSF receptor.

In some embodiments, the amino acid sequence for a cytokine such as GM-CSF has at least 80, 85, 87, 89, 90, 91, 92, 93, 94, 95, 96, 97, 98, 99% or more sequence identity to the sequence presented as SEQ ID NO:11, when compared and aligned for maximum correspondence.

5.6 COMBINATION THERAPIES

In one embodiment, cells are engineered (genetically modified) to enhance expression of an antigen associated with an immune response to prostate cancer (e.g., a filamin-B peptide) and are either further engineered to express one or more proteins that enhance the immune response to prostate cancer, e.g., a cytokine such as GM-CSF or are administered in combination with different cells which are either further engineered to express one or more proteins that enhance the immune response to prostate cancer, e.g., a cytokine such as GM-CSF.

In one embodiment, a population of cells that expresses one, two, three, four, five, six, seven, or more filamin-B peptides according to the present invention is administered to the patient as part of a cellular vaccine. The filamin-B peptide-expressing cell may be the same as or different from the cell that expresses a cytokine such as GM-CSF. In another embodiment of the invention, the cellular vaccine comprises one, two, three, four, five, six, seven, or more filamin-B peptides as described herein. The cellular vaccine may further comprise an immune enhancing agent (e.g. a cytokine such as GM-CSF, an adjuvant such as lipid A, or a derivative thereof, a CpG containing nucleic acid, alum, or the like).

Cells can be enhanced for filamin-B peptide expression by various methods known to those skilled in the art. For example, cells may be transduced with a vector which encodes the filamin-B peptide(s), operatively linked to the filamin-B peptide coding sequence. Suitable promoters are known and available to those skilled in the art. A vector useful for transducing the cells can be any vector that is effective to result in the enhanced expression of one or more filamin-B peptides. In one embodiment the vector is a viral vector, e.g., a retroviral vector such as a lentiviral vector, an adenoviral vector or an adeno-associated viral vector. A vector may also be used to transduce the cells with a coding region for a protein that enhances the immune response to cancer in the subject, e.g., a cytokine such as GM-CSF. This coding region and the filamin-B peptide coding region can be located on one vector or on separate vectors and introduced into the same or different cells. If on separate vectors, the separate vectors may be of the same origin (e.g. retroviral) or of different origins. In one embodiment, the cell is first transduced with a vector coding for a filamin-B peptide and then transduced with a vector coding for GM-CSF. In another embodiment, the cell is first transduced with a vector coding for at least one protein that enhances an immune response to prostate cancer and then transduced with a vector coding for filamin-B.

Another embodiment of the invention is a method of increasing an immune response to a tumor cell and/or a filamin-B peptide comprising: administering genetically modified cytokine-expressing cells to a prostate cancer patient wherein an improved therapeutic outcome results. Another embodiment of the invention is a method of increasing an immune response to a tumor cell and/or a filamin-B peptide comprising: administering genetically modified cytokine-expressing cells that exhibit enhanced expression of a filamin-B peptide to a prostate cancer patient wherein after said administration, the patient's immune response to prostate cancer is increased. Yet another embodiment of the invention is a method of increasing an immune response to a tumor cell and a filamin-B peptide comprising: administering genetically modified cells that exhibit enhanced expression of a cytokine (e.g., GM-CSF) to a prostate cancer patient, wherein after administration, the mammal's immune response to the filamin-B peptide is increased. In one embodiment, the increased immune response is humoral. In yet another embodiment, the increased immune response is cellular. In still a further embodiment, the increased immune response is both cellular and humoral. In a preferred aspect of the invention, after administration of genetically modified cytokine-producing cells, the growth of the prostate cancer cells is inhibited.

Assays for determining if the cells express detectable levels of a filamin-B peptide and/or if the immune response to beta filamin has changed following administration of a cytokine-expressing cell vaccine include, but are not limited to, ELISA, Western blot, Immunofluorescence assay (IFA), FACS or Electrochemiluminescence (ECL).

In still another aspect, the invention provides a method for increasing an immune response to a tumor cell and/or a filamin-B peptide comprising administering genetically modified cytokine-expressing cells and CTLs that have been contacted to cells expressing the class I MHC receptor HLA-A2 with a filiamin-B peptide of the invention bound thereto to a prostate cancer patient, wherein an improved therapeutic outcome results. Another embodiment of the invention is a method of increasing an immune response to a tumor cell and/or a filamin-B peptide comprising: administering genetically modified cytokine-expressing cells and CTLs that have been contacted to cells expressing the class I MHC receptor HLA-A2 with a filiamin-B peptide of the invention bound thereto to a prostate cancer patient wherein after said administration, the patient's immune response to prostate cancer is increased. Yet another embodiment of the invention is a method of increasing an immune response to a tumor cell and a filamin-B peptide comprising: administering genetically modified cells that exhibit enhanced expression of a cytokine (e.g., GM-CSF) and CTLs that have been contacted to cells expressing the class I MHC receptor HLA-A2 with a filiamin-B peptide of the invention bound thereto to a prostate cancer patient, wherein after administration, the mammal's immune response to the filamin-B peptide is increased. In one embodiment, the increased immune response is humoral. In yet another embodiment, the increased immune response is cellular. In still a further embodiment, the increased immune response is both cellular and humoral. In a preferred aspect of the invention, after administration of genetically modified cytokine-producing cells and CTLs that have been contacted to cells expressing the class I MHC receptor HLA-A2 with a filiamin-B peptide of the invention bound thereto, the growth of the prostate cancer cells is inhibited.

6. EXAMPLES

The present invention is described by reference to the following Examples, which are offered by way of illustration and are not intended to limit the invention in any manner. Standard techniques well known in the art or the techniques specifically described below are utilized. It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

Exemplary methods for producing recombinant viral vectors useful for making genetically altered tumor cells that express GM-CSF, methods for using the genetically altered tumor cells that express GM-CSF in cancer therapies, particularly prostate cancer therapies, are extensively described in U.S. Patent Application Publication No. 2006/0057127, incorporated by reference in its entirety, and will not be reproduced below.

6.1 Example 1

Identification of Filamin-B Peptides that Bind MHC I Receptor HLA-A2

This example describes identification of 9-mer peptides selected from the filamin-B polypeptide that bind to the class I MHC receptor HLA-A2. First, seven filamin B peptides that were predicted to bind to HLA-A2 were identified using the prediction programs PAProC (Nussbaum A K et al., 2001, Immunogenetics 53: 87, and Kuttler C et al., 2000, J. Mol. Biol. 298:417), UniProt (Sasson O et al., 2006, Protein Sci. 15:1557, and Pospisil P. Et al., 2006, BMC Bioinformatics. 20:354), NetChop (Nielsen M. Et al., 2005, Immunogenetics. 57:33-41, and Kcsmir C. ct al., 2002, Protein Eng. 15:287), EpiJen (Doytchinova I A et al, 2006, BMC Bioinformatics. 2006, 13:131) and MHCPred (Guan P. et al., Appl Bioinformatics. 2006; 5(1):55-61, and Hattotuwagama C K et al., 2004, J Mol Graph Model. 22:195) from the filamin B sequence identified with Accession No. NP.sub.—001448 (SEQ ID NO[H]:1). The seven peptides are shown in Table 1, below:

TABLE 1

| Filamin B peptide #1 | LILGLVWTL |
| Filamin B peptide #2 | GLVEPVNMV |
| Filamin B peptide #3 | GLAPLEVRV |
| Filamin B peptide #4 | SLQESGLKV |
| Filamin B peptide #5 | RLIALLEVL |

TABLE 1-continued

| | |
|---|---|
| Filamin B peptide #6 | GQGDVMVFV |
| Filamin B peptide #7 | KLILGLVWT |

Next, each of the seven peptides were chemically synthesized (Biosynthesis, Lewisville, Tex.) by standard 9-fluorenylmethyl-oxycarbonyl chemistry, purified to >90% purity by reverse-phase chromatography, and validated by mass-spectrometry for molecular weight. The peptides were then resuspended in PBS+0.1% BSA and stored at −20° C. or at −70° C. prior to their use in the binding assays described below.

To confirm that the seven peptides bind HLA-A2, T2 cells, a TAP-deficient human B-×T-lymphoblastoid hybrid cell line, were used to evaluate HLA-A2-specific peptide binding. In the assay, T2 cells were washed and resuspended in serum-free AIM-V medium (Gibco-Life Technologies) to a final concentration of $1 \times 10^6$ cells/ml and transferred into a 24-well tissue culture plate. Cells were pulsed with a selected filamin-B peptide at various concentrations (0-200 μg/ml) or influenza virus protein matrix peptide as positive control (residues 58-66; GILGFVFTL (SEQ ID NO.:12); 30 μg/ml) plus 3 μg human β2-microglobulin (Sigma, St. Louis, Mo.) and incubated at 37° C., 5% $CO_2$ in humidified air. Following overnight incubation, the cells were washed and stained with mouse anti-human HLA-A2 monoclonal antibody for 15 min at 4° C.

After washing, the cells were incubated with goat anti-mouse IgG (F(ab')$_2$)-FITC (Sigma, St. Louis, Mo.) for 15 min at 4° C. The cells were washed and analyzed on a FACSort flow cytometer with CellQuest v2.1 software (Becton-Dickson, San Jose, Calif.). The fluorescence index (mean channel fluorescence of T2 cells pulsed with the peptide plus β$_2$ microglobulin/mean channel fluorescence of T2 cells pulsed with β$_2$ microglobulin only) was calculated to determine the up-regulation of HLA-A2 expression on T2 cells caused by peptide pulsing. Up-regulation of HLA-A2 expression correlates with binding of HLA-A2 by the filamin-B peptides.

Results of these experiments are presented in Table 2, below.

TABLE 2

| | Assay #1 | Assay #2 | Average | SE |
|---|---|---|---|---|
| Influenza virus peptide | 4.17 | 3.57 | 3.87 | 0.24 |
| Filamin B peptide #1 | 3.46 | 2.17 | 2.82 | 0.53 |
| Filamin B peptide #2 | 3.17 | 2.68 | 2.93 | 0.20 |
| Filamin B peptide #3 | 4.21 | 3.64 | 3.93 | 0.23 |
| Filamin B peptide #4 | 1.96 | 1.61 | 1.79 | 0.14 |
| Filamin B peptide #5 | 2.75 | 2.5 | 2.63 | 0.10 |
| Filamin B peptide #6 | 2.67 | 1.96 | 2.32 | 0.29 |
| Filamin B peptide #7 | 1.38 | 1.25 | 1.32 | 0.05 |

To test the stability of the interaction between the peptides and HLA-A2, fluorescence was monitored for several hours following the addition of brefeldin A to the assay. By adding brefeldin A, synthesis and transport of new HLA-A2 molecules to the cell surface was interrupted so that any signal detected was from HLA-A2 receptors already present on the cell surface prior to addition of brefeldin A. Results from these experiments are presented as Table 3, below.

TABLE 3

| | | Time After Brefeldin A trt | | | | | |
|---|---|---|---|---|---|---|---|
| | | 0 hr (F.I.) | 2 hr | 4 hr | 6 hr | 8 hr | 18 hr |
| Assay #1 | T2 + Filamin B peptide #1 | 3.46 | 3.17 | 3.17 | 3.32 | 3.22 | 2.45 |
| Assay #2 | T2 + Filamin B peptide #1 | 2.17 | 2.17 | 2.16 | 1.83 | 1.57 | 1.35 |
| Average | | 2.82 | 2.67 | 2.67 | 2.58 | 2.40 | 1.90 |
| SE | | 0.53 | 0.41 | 0.41 | 0.61 | 0.67 | 0.45 |
| Assay #1 | T2 + Filamin B peptide #2 | 3.17 | 2.61 | 2.39 | 1.9 | 1.68 | 1.1 |
| Assay #2 | T2 + Filamin B peptide #2 | 2.68 | 2.2 | 1.94 | 1.49 | 1.23 | 1 |
| Average | | 2.93 | 2.41 | 2.17 | 1.70 | 1.46 | 1.05 |
| SE | | 0.20 | 0.17 | 0.18 | 0.17 | 0.18 | 0.04 |
| Assay #1 | T2 + Filamin B peptide #3 | 4.21 | 4.3 | 4.22 | 4.27 | 4.01 | 3.1 |
| Assay #2 | T2 + Filamin B peptide #3 | 3.64 | 3.33 | 3.35 | 2.94 | 2.89 | 2.1 |
| Average | | 3.93 | 3.82 | 3.79 | 3.61 | 3.45 | 2.60 |
| SE | | 0.23 | 0.40 | 0.36 | 0.54 | 0.46 | 0.41 |
| Assay #1 | T2 + Filamin B peptide #4 | 1.96 | 1.43 | 1.43 | 1.18 | 1.09 | 1.1 |
| Assay #2 | T2 + Filamin B peptide #4 | 1.61 | 1.37 | 1.13 | 1 | 1 | 1 |
| Average | | 1.79 | 1.40 | 1.28 | 1.09 | 1.05 | 1.05 |
| SE | | 0.14 | 0.02 | 0.12 | 0.07 | 0.04 | 0.04 |
| Assay #1 | T2 + Filamin B peptide #5 | 2.75 | 2.87 | 2.52 | 2.86 | 2.82 | 2.15 |
| Assay #2 | T2 + Filamin B peptide #5 | 2.5 | 2.5 | 2.5 | 2.03 | 1.97 | 1.55 |
| Average | | 2.63 | 2.69 | 2.51 | 2.45 | 2.40 | 1.85 |
| SE | | 0.10 | 0.15 | 0.01 | 0.34 | 0.35 | 0.24 |
| Assay #1 | T2 + Filamin B peptide #6 | 2.67 | 1.74 | 1.65 | 1.23 | 1.09 | 1.1 |
| Assay #2 | T2 + Filamin B peptide #6 | 1.96 | 1.6 | 1.29 | 1 | 1 | 1 |
| Average | | 2.32 | 1.67 | 1.47 | 1.12 | 1.05 | 1.05 |
| SE | | 0.29 | 0.06 | 0.15 | 0.09 | 0.04 | 0.04 |
| Assay #1 | T2 + Filamin B peptide #7 | 1.38 | 1.24 | 1.22 | 1.09 | 1.09 | 1.25 |
| Assay #2 | T2 + Filamin B peptide #7 | 1.25 | 1.07 | 1.1 | 1 | 1 | 1 |
| Average | | 1.32 | 1.16 | 1.16 | 1.05 | 1.05 | 1.13 |
| SE | | 0.05 | 0.07 | 0.05 | 0.04 | 0.04 | 0.10 |
| Assay #1 | T2 + Influenza virus peptide | 4.17 | 4.09 | 4.04 | 4 | 3.86 | 3.85 |
| Assay #2 | T2 + Influenza virus peptide | 3.57 | 3.4 | 3.52 | 2.86 | 2.86 | 2 |
| Average | | 3.87 | 3.75 | 3.78 | 3.43 | 3.36 | 2.93 |
| SE | | 0.24 | 0.28 | 0.21 | 0.47 | 0.41 | 0.76 |
| Assay #1 | T2 + MAGE 3 peptide | 3 | 2.87 | 2.83 | 2.95 | 2.41 | 1.65 |
| Assay #2 | T2 + MAGE 3 peptide | 2.46 | 2.4 | 2.48 | 1.86 | 1.63 | 0.7 |

TABLE 3-continued

|  | Time After Brefeldin A trt | | | | | |
|---|---|---|---|---|---|---|
|  | 0 hr (F.I.) | 2 hr | 4 hr | 6 hr | 8 hr | 18 hr |
| Average | 2.73 | 2.64 | 2.66 | 2.41 | 2.02 | 1.18 |
| SE | 0.22 | 0.19 | 0.14 | 0.44 | 0.32 | 0.39 |

As shown in Tables 2 and 3, each of the seven peptides were able to bind to HLA-A2 and up-regulated expression of HLA-A2. Peptides 1, 3, and 5 exhibited the greatest upregulation, peptides 2, 4, and 6 exhibited moderate upregulation, while peptide 7 upregulated HLA-A2 weakly. Thus, this example demonstrates that the seven filamin-B peptides each could bind the HLA-A2 receptor, though one peptide bound quite weakly.

6.2 Example 2

Detecting Activation of Cytotoxic T Lymphocytes in IFN-γ Assays

This example provides an exemplary method for detecting activation of cytotoxic T lymphocytes (CTLs) by monitoring IFN-γ expression by the CTLs in response to exposure to an appropriate antigen, e.g., a filamin-B peptide presented on an MHC I receptor.

First, peripheral blood monocytic cells (PBMCs) are isolated from a subject to be assessed for cellular immune response against a filamin-B peptide and CD8+ cells are isolated by fluorescence activated cell sorting (FACS). The CD8+ cells are then incubated with, e.g., T2 cells loaded with the filamin-B peptide to be assessed, produced as described above, and in the presence of suitable cytokines for expanding the CTL population.

IFN-γ release by the CTLs is measured using an IFN-γ ELISA kit (PBL-Biomedical Laboratory, Piscataway, N.J.). Briefly, purified IFN-γ as standards or culture supernates from the CTL-T2 co-culture are transferred into wells of a 96-well plate pre-coated with a monoclonal anti-human IFN-γ capture antibody and incubated for 1 h in a closed chamber at 24° C. After washing the plate with PBS/0.05% Tween 20, biotin anti-human IFN-γ antibody is added to the wells and incubated for 1 h at 24° C. The wells are washed and then developed by incubation with streptavidin horseradish peroxidase conjugate and TMB substrate solution. Stop solution is added to each well and the absorbance is determined at 450 nm with a SpectraMAX Plus plate reader (Stratagene, La Jolla, Calif.). The amount of cytokine present in the CTL culture supernatants is calculated based on the IFN-γ standard curve.

6.3 Example 3

Detecting Activation of Cytotoxic T Lymphocytes in Proliferation Assays

This example provides an exemplary method for detecting activation of cytotoxic T lymphocytes (CTLs) by CTL proliferation in response to exposure to an appropriate antigen, e.g., a filamin-B peptide presented on an MHC I receptor.

First, peripheral blood monocytic cells (PBMCs) are isolated from a subject to be assessed for cellular immune response against a filamin-B peptide and CD8+ cells are isolated by fluorescence activated cell sorting (FACS). The CD8+ cells are then incubated with, e.g., T2 cells loaded with the filamin-B peptide to be assessed, produced as described above.

Next, the samples are incubated for 12 hours, then 20 μl of 3H-thymidine is added to each well and the sample incubated for an additional 12 hours. Cells are harvested and the plate is read in a beta counter to determine the amount of unincorporated 3H-thymidine.

6.4 Example 4

Detecting Activation of Cytotoxic T Lymphocytes in Effector Assays

This example provides an exemplary method for detecting activation of cytotoxic T lymphocytes (CTLs) by monitoring lysis of cells displaying an appropriate antigen, e.g., a filamin-B peptide presented on an MHC I receptor.

The cytotoxic activity of the CTLs is measured in a standard $^{51}$Cr-release assay. Effector cells (CTLs) are seeded with $^{51}$Cr-labeled target cells ($5 \times 10^3$ cells/well) at various effector:target cell ratios in 96-well U-bottom microtiter plates. Plates are incubated for 4 h at 37° C., 5% $CO_2$. The $^{51}$Cr-release is measured in 100 μl supernatant using a Beckman LS6500 liquid scintillation counter (Beckman Coulter, Brea, Calif.). The percent specific cell lysis is calculated as [(experimental release−spontaneous release)/(maximum release−spontaneous release)]. Maximum release is obtained from detergent-released target cell counts and spontaneous release from target cell counts in the absence of effector cells.

While many specific examples have been provided, the above description is intended to illustrate rather than limit the invention. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. Citation of these documents is not an admission that any particular reference is "prior art" to this invention.

SEQ ID No.: 1

```
  1 mpvtekdlae dapwkkiqqn tftrwcnehl kcvnkrignl qtdlsdglrl iallevlsqk 61 rmyrkyhqrp tfrqmqlenv svalefldre siklvsidsk aivdgnlkli lglvwtlilh 121 ysismpvwed egdddakkqt pkqrllgwiq nkipylpitn fnqnwqdgka lgalvdscap
```

```
 181 glcpdweswd pqkpvdnare amqqaddwlg vpqvitpeei ihpdvdehsv mtylsqfpka
 241 klkpgaplkp klnpkkaray grgieptgnm vkqpakftvd tisagqgdvm vfvedpegnk
 301 eeaqvtpdsd knktysveyl pkvtglhkvt vlfagqhisk spfevsvdka ggdaskvtak
 361 gpgleavgni ankptyfdiy tagagvgdig vevedpqgkn tvellvedkq nqvyrcvykp
 421 mqpqphvvki ffagdtipks pfvvqvgeac npnacrasgr glqpkgvrir ettdfkvdtk
 481 aagsgelgvt mkgpkgleel vkqkdfldgv yafeyypstp qrysiaitwg ghhipkspfe
 541 vqvgpeagmq kvrawgpglh ggivgrsadf vvesigsevg slgfaiegps qakieyndqn
 601 dgscdvkywp kepgeyavhi mcddedikds pymafihpat ggynpdlvra ygpgleksgc
 661 ivnnlaeftv dpkdagkapl kifaqdgegq ridiqmknrm dgtyacsytp vkaikhtiav
 721 vwggvniphs pyrvnigqgs hpqkvkvfgp gversglkan epthftvdct eagegdvsvg
 781 ikcdarvlse deedvdfdii hnandtftvk yvppaagryt ikvlfasqei paspfrvkvd
 841 pshdaskvka egpglskagv engkpthftv ytkgagkapl nvqfnsplpg davkdldiid
 901 nydyshtvky tptqqgnmqv lvtyggdpip kspftvgvaa pldlskikln glenrvevgk
 961 dqeftvdtrg aggqgkldvt ilspsrkvvp clvtpvtgre nstakfipre eglyavdvty
1021 dghpvpgspy tveaslppdp skvkahgpgl egglvgkpae ftidtkgagt gglgltvegp
1081 ceakiecsdn gdgtcsvsyl ptkpgeyfvn ilfeevhipg spfkadiemp fdpskvvasg
1141 pglehgkvge aglllsvdcse agpgalglea vsdsgtkaev siqnnkdgty avtyvpltag
1201 mytltmkygg elvphfparv kvepavdtsr ikvfgpgieg kdvfreattd ftvdsrpltq
1261 vggdhikahi anpsgastec fvtdnadgty qveytpfekg lhvvevtydd vpipnspfkv
1321 avtegcqpsr vqaqgpglke aftnkpnvft vvtrgagigg lgitvegpse skincrdnkd
1381 gscsaeyipf apgdydvnit yggahipgsp frvpvkdvvd pskvkiagpg lgsgvrarvl
1441 qsftvdsska glaplevrvl gprglvepvn vvdngdgtht vtytpsqegp ymvsvkyade
1501 eiprspfkvk vlptydaskv tasgpglssy gvpaslpvdf aidardageg llavqitdqe
1561 gkpkraivhd nkdgtyavty ipdktgrymi gvtyggddip lspyriratq tgdaskclat
1621 gpgiastvkt geevgfvvda ktagkgkvtc tvltpdgtea eadvienedg tydifytaak
1681 pgtyviyvrf ggvdipnspf tvmatdgevt aveeapvnac ppgfrpwvte eayvpvsdmn
1741 glgfkpfdlv ipfavrkgei tgevhmpsgk tatpeivdnk dgtvtvryap tevglhemhi
1801 kymgshipes plqfyvnypn sgsvsaygpg lvygvankta tftivtedag eggldlaieg
1861 pskaeiscid nkdgtctvty lptlpgdysi lvkyndkhip gspftakitd dsrrcsqvkl
1921 gsaadflldi setdlsslta sikapsgrde pcllkrlpnn higisfipre vgehlvsikk
1981 ngnhvanspv simvvqseig darrakvygr glsegrtfem sdfivdtrda gyggislave
2041 gpskvdiqte dledgtckvs yfptvpgvyi vstkfadehv pgspftvkis gegrvkesit
2101 rtsrapsvat vgsicdlnlk ipeinssdms ahvtspsgrv teaeivpmgk nshcvrfvpq
2161 emgvhtvsvk yrgqhvtgsp fqftvgplge ggahkvragg pglergeagv paefsiwtre
2221 agagglsiav egpskaeitf ddhkngscgv syiaqepgny evsikfndeh ipespylvpv
2281 iapsddarrl tvmslqesgl kvnqpasfai rlngakgkid akvhspsgav eechvselep
2341 dkyavrfiph engvhtidvk fngshvvgsp fkvrvgepgq agnpalvsay gtgleggttg
2401 iqseffintt ragpgtlsvt iegpskvkmd cqetpegykv mytpmapgny lisvkyggpn
```

```
2461 hivgspfkak vtgqrlvspg sanetssilv esvtrsstet cysaipkass daskvtskga 2521 glskafvgqk ssflvdcska gsnmlligvh gpttpceevs mkhvgnqqyn vtyvvkergd 2581 yvlavkwgee hipgspfhvt vp
```

---

What is claimed is:

1. A method for determining whether a cellular immune response against cancer cells has been induced in a subject, comprising:
    (a) contacting cytotoxic T lymphocytes (CTLs) from the subject to cells that express an HLA-A2 class I MHC receptor, wherein the HLA-A2 receptor has a peptide bound thereto, wherein the peptide is GLAPLEVRV (SEQ ID NO: 4); and
    (b) detecting activation of the CTLs by the cells that express the HLA-A2 receptor, wherein detecting said activation indicates that a cellular immune response against prostate cancer has been induced in the subject.

2. The method of claim 1, wherein the cells that express the HLA-A2 receptor are primate cells, canine cells, rodent cells, lagomorph cells, bovine cells, equine cells, or insect cells.

3. The method of claim 1, wherein the cells that express the HLA-A2 receptor are human cells, mouse cells, rat cells, or hamster cells.

4. The method of claim 1, wherein the cells that express the HLA-A2 receptor are human cells.

5. The method of claim 1, wherein the cells that express the HLA-A2 receptor are from an immortalized cell line.

6. The method of claim 1, wherein the cells that express the HLA-A2 receptor are T2 cells.

7. The method of claim 1, wherein activation of the CTLs is detected by detecting secretion of IFN-γ by the CTLs.

8. The method of claim 1, wherein activation of the CTLs is detected by detecting proliferation of the CTLs.

9. The method of claim 1, wherein activation of the CTLs is detected by detecting lysis of the cells expressing the HLA-A2 receptor by the CTLs.

10. The method of claim 1, wherein the cancer cells are prostate cancer cells.

11. A method for determining whether a cellular immune response effective to treat a symptom of prostate cancer in a subject has been induced in the subject, comprising:
    (a) contacting in vitro CTLs from the subject to cells that express an HLA-A2 class I MHC receptor, wherein the HLA-A2 receptor has a peptide bound thereto, wherein the peptide is, GLAPLEVRV (SEQ ID NO: 4); and
    (b) detecting activation of the CTLs by the cells that express the HLA-A2 receptor, wherein detecting said activation indicates that a cellular immune response effective to treat a symptom of prostate cancer has been induced in the subject.

12. The method of claim 11, wherein activation of the CTLs is detected by detecting secretion of IFN-γ by the CTLs.

13. The method of claim 11, wherein activation of the CTLs is detected by detecting proliferation of the CTLs.

14. The method of claim 11, wherein activation of the CTLs is detected by detecting lysis of the cells expressing the HLA-A2 receptor by the CTLs.

15. The method of claim 11, wherein the cells that express the HLA-A2 receptor are primate cells, canine cells, rodent cells, lagomorph cells, bovine cells, equine cells, or insect cells.

16. The method of claim 11, wherein the cells that express the HLA-A2 receptor are human cells, mouse cells, rat cells, or hamster cells.

17. The method of claim 11, wherein the cells that express the HLA-A2 receptor are human cells.

18. The method of claim 11, wherein the cells that express the HLA-A2 receptor are from an immortalized cell line.

19. The method of claim 11, wherein the cells that express the HLA-A2 receptor are T2 cells.

* * * * *